(12) United States Patent
Gunderson et al.

(10) Patent No.: US 11,375,905 B2
(45) Date of Patent: Jul. 5, 2022

(54) PERFORMING ONE OR MORE PULSE TRANSIT TIME MEASUREMENTS BASED ON AN ELECTROGRAM SIGNAL AND A PHOTOPLETHYSMOGRAPHY SIGNAL

(71) Applicant: Medtronic, Inc., Minneapolis, MN (US)

(72) Inventors: Bruce D. Gunderson, Plymouth, MN (US); Avram Scheiner, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 141 days.

(21) Appl. No.: 16/691,183

(22) Filed: Nov. 21, 2019

(65) Prior Publication Data
US 2021/0153751 A1    May 27, 2021

(51) Int. Cl.
| | | |
|---|---|---|
| *A61B 5/00* | (2006.01) | |
| *A61B 5/0205* | (2006.01) | |
| *A61B 5/352* | (2021.01) | |
| *A61B 5/11* | (2006.01) | |
| *A61B 5/021* | (2006.01) | |
| *A61B 5/024* | (2006.01) | |

(52) U.S. Cl.
CPC .......... *A61B 5/0205* (2013.01); *A61B 5/1116* (2013.01); *A61B 5/1126* (2013.01); *A61B 5/352* (2021.01); *A61B 5/681* (2013.01); *A61B 5/7275* (2013.01); *A61B 5/02125* (2013.01); *A61B 5/02427* (2013.01); *A61B 5/6826* (2013.01); *A61B 2562/0219* (2013.01)

(58) Field of Classification Search
None
See application file for complete search history.

(56) References Cited

U.S. PATENT DOCUMENTS

| | | |
|---|---|---|
| 5,368,040 A | 11/1994 | Carney |
| 5,857,975 A | 1/1999 | Golub |
| 6,024,704 A | 2/2000 | Meador et al. |
| 6,409,675 B1 | 6/2002 | Turcott |
| 7,029,447 B2 | 4/2006 | Rantala |
| 8,475,370 B2 | 7/2013 | McCombie et al. |

(Continued)

OTHER PUBLICATIONS

Bereski-Reguig et al., "A New System for Measurement of the Pulse Transit Time, the Pulse Wave Velocity and its Analysis," World Scientific, Journal of Mechanics in Medicine and Biology, vol. 17, No. 1, Apr. 8, 2016, 21 pp.

(Continued)

*Primary Examiner* — Nathan J Jenness
*Assistant Examiner* — Skylar Lindsey Christianson
(74) *Attorney, Agent, or Firm* — Shumaker & Sieffert, P.A.

(57) ABSTRACT

This disclosure is directed to devices, systems, and techniques for monitoring a patient condition. In some examples, a medical device system includes processing circuitry configured to determine a plurality of pulse transit time (PTT) intervals, determine, based on an accelerometer signal, a posture of a patient from a plurality of postures corresponding to each PTT interval of the plurality of PTT intervals, classify each PTT interval of the plurality of PTT intervals based on the respective posture of the patient corresponding to the respective PTT interval, and monitor, based on the classified plurality of PTT intervals, a patient condition.

20 Claims, 11 Drawing Sheets

(56) References Cited

U.S. PATENT DOCUMENTS

| | | |
|---|---|---|
| 8,521,281 B2 | 8/2013 | Patel et al. |
| 2002/0058969 A1 | 5/2002 | Noren et al. |
| 2006/0041281 A1 | 2/2006 | Von Arx et al. |
| 2007/0129765 A1 | 6/2007 | Gilkerson et al. |
| 2008/0183083 A1* | 7/2008 | Markowitz .......... A61B 5/0285 600/484 |
| 2009/0281399 A1 | 11/2009 | Keel et al. |
| 2011/0224498 A1 | 9/2011 | Banet et al. |
| 2013/0096449 A1* | 4/2013 | Patel ....................... A61N 1/37 600/516 |
| 2013/0123617 A1 | 5/2013 | Sola i Caros et al. |
| 2014/0276928 A1 | 9/2014 | Vanderpool et al. |
| 2015/0164437 A1* | 6/2015 | McCombie ........... A61B 5/1114 600/301 |
| 2015/0283383 A1 | 10/2015 | Ternes et al. |
| 2016/0310031 A1 | 10/2016 | Sarkar |
| 2017/0119263 A1* | 5/2017 | Hill ...................... A61B 5/7221 |

OTHER PUBLICATIONS

PCT/US2020/058762, The International Search Report and Written Opinion, dated Feb. 25, 2021, 10pages.

* cited by examiner

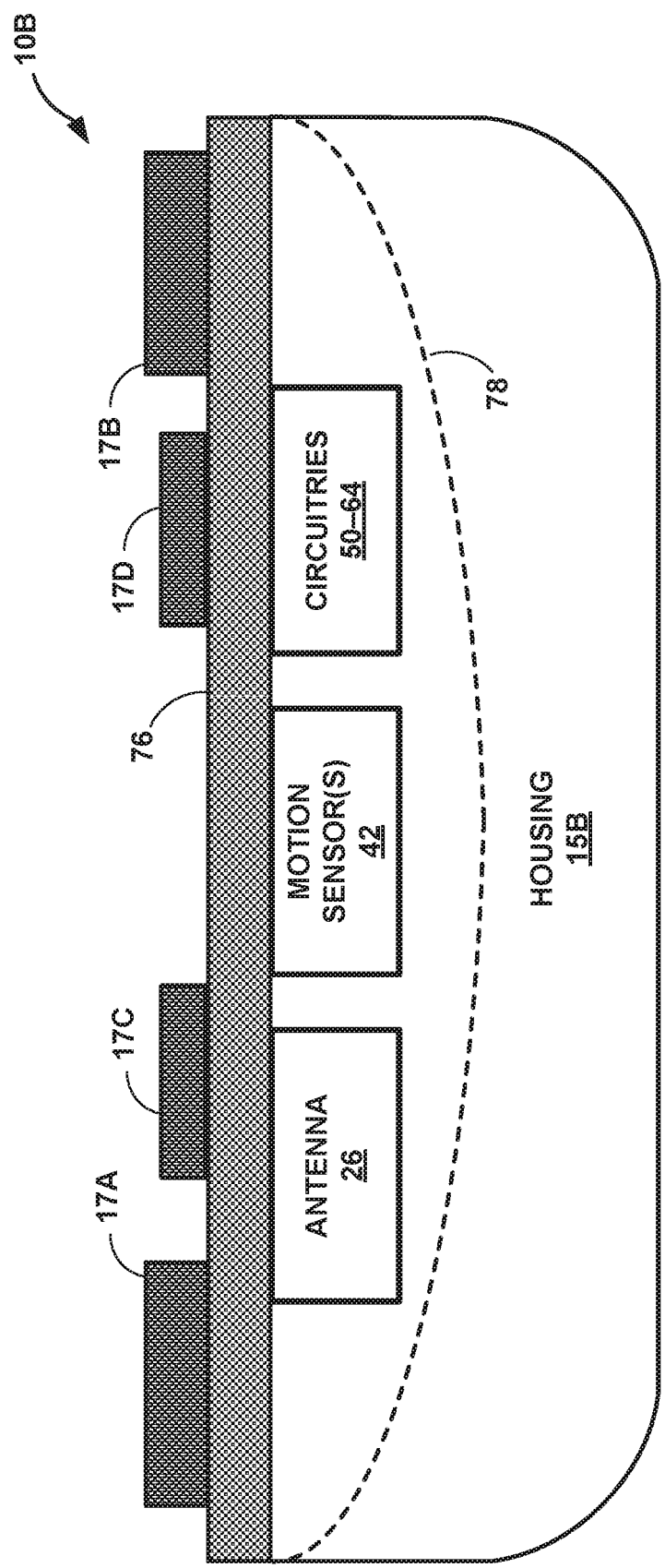

PERFORMING ONE OR MORE PULSE TRANSIT TIME MEASUREMENTS BASED ON AN ELECTROGRAM SIGNAL AND A PHOTOPLETHYSMOGRAPHY SIGNAL

TECHNICAL FIELD

The disclosure relates generally to medical device systems and, more particularly, medical device systems configured to monitor patient parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in generally evaluating patient health.

SUMMARY

In general, the disclosure is directed to devices, systems, and techniques for monitoring a patient condition based on one or more pulse transit time (PTT) intervals. For example, a length of a PTT interval may be correlated with a blood pressure of a patient. As such, a trend relating to the length of a set of PTT intervals may indicate a trend in a blood pressure of the patient. It may be beneficial to monitor blood pressure in order to manage one or more patient conditions, such as hypertension. As another example, detecting an intermittent low blood pressure event may indicate an onset of a pre-syncope or a syncope event.

In some examples, an implantable medical device (IMD) collects an electrogram (EGM) signal of a patient. EGM signals, in some cases, may indicate one or more events of a heart cycle such as ventricular depolarizations, atrial depolarizations, or any combination thereof. For example, an R-wave may represent a ventricular depolarization which causes the heart to contract and pump a volume of blood through the vasculature of the patient. Additionally, the IMD may collect an accelerometer signal which indicates a posture and/or a movement level of the patient. In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. The accelerometer signal may indicate which posture of a set of postures that the patient is occupying, the set of postures including a supine position, a prone position, a lying on a side position, a sitting position, and a standing position, as examples.

A wearable device may collect a photoplethysmography (PPG) signal of the patient. The PPG signal may represent a detected pulse at the location of the wearable device. The PPG signal may be correlated with an amount of blood that is flowing at the location of the wearable device. For example, if blood is flowing at a first rate at a first time and blood is flowing at a second rate at a second time, the second rate being greater than the first rate, a magnitude of the PPG signal at the second time may be greater than a magnitude of the PPG signal at the first time. During a heartbeat, the ventricles of the heart may contract, causing the heart to push a volume of blood into the vasculature of the patient. Processing circuitry may calculate a PTT interval by determining an amount of time between an R-wave of the EGM signal and a peak or other feature of the PPG signal that indicates a pulse, which occurs after the R-wave and before a subsequent and consecutive R-wave of the EGM signal. The wearable device may be placed on an extremity of the patient (e.g., a wrist, a finger, an ankle, or a toe). As such, a PTT interval may represent an amount of time that it takes for blood to travel from the ventricle to the extremity on which the wearable device is attached during a heartbeat.

The techniques of this disclosure may provide one or more advantages. For example, it may be beneficial to monitor a blood pressure of a patient by calculating one or more PTT intervals of the patient based on an EGM signal collected by an IMD and a PPG signal collected by a wearable device since the IMD may be implanted in the patient for an extended period of time and the patient may wear the wearable device for an extended period of time. In this way, a medical device system including the IMD and the wearable device may calculate a plurality of PTT intervals of the patient over an extended period of time (e.g., days, weeks, months, or years) and identify long-term trends in the patient's blood pressure based on the plurality of PTT intervals. Additionally, it may be beneficial for processing circuitry to identify trends relating to the plurality of PTT intervals based on one or more of a posture, an activity level, and a body angle of the patient. For example, based on the accelerometer signal, the processing circuitry may identify a set of PTT intervals of the plurality of PTT intervals that occur while the patient is occupying a posture. In turn, the processing circuitry may identify a trend in the set of PTT intervals, while posture is held constant across the set of PTT intervals.

In some examples, a medical device system includes a medical device including a plurality of electrodes configured to collect an electrogram (EGM) signal of a patient, wherein the EGM signal includes a plurality of depolarizations and an accelerometer configured to collect an accelerometer signal that indicates which posture of a set of postures that the patient is occupying. Additionally, the medical device system includes a wearable device configured to collect a photoplethysmography (PPG) signal of the patient, wherein the PPG signal includes a plurality of PPG features indicating the occurrence of a cardiac pulse and processing circuitry in communication with a memory. The processing circuitry is configured to determine a plurality of pulse transit time (PTT) intervals, wherein a PTT interval of the plurality of PTT intervals corresponds to each depolarization of the plurality of depolarizations, wherein each PTT interval of the plurality of PTT intervals represents an amount of time between the respective depolarization of the set of depolarizations and a PPG feature of the plurality of PPG features that occurs after the respective depolarization and before a subsequent depolarization of the plurality of depolarizations, determine, based on the accelerometer signal, a posture of the patient from a plurality of postures corresponding to each PTT interval of the plurality of PTT intervals, classify each PTT interval of the plurality of PTT intervals based on the respective posture of the patient corresponding to the respective PTT interval, and monitor, based on the classified plurality of PTT intervals, a patient condition.

In some examples, a method including collecting, using a plurality of electrodes of a medical device, an electrogram (EGM) signal of a patient, wherein the EGM signal includes a plurality of depolarizations, collecting, using an accelerometer of the medical device, an accelerometer signal that indicates which posture of a set of postures that the patient is occupying, and collecting, using a wearable device, a photoplethysmography (PPG) signal of the patient, wherein the PPG signal includes a plurality of PPG features indicating the occurrence of a cardiac pulse. Additionally, the method includes determining, using processing circuitry in communication with a memory, a plurality of pulse transit time (PTT) intervals, wherein a PTT interval of the plurality of PTT intervals corresponds to each depolarization of the plurality of depolarizations, wherein each PTT interval of the plurality of PTT intervals represents an amount of time between the respective depolarization of the set of depolarizations and a PPG feature of the plurality of PPG features that occurs after the respective depolarization and before a subsequent depolarization of the plurality of depolarizations, determining, based on the accelerometer signal, a posture of the patient from a plurality of postures corresponding to each PTT interval of the plurality of PTT intervals, classifying each PTT interval of the plurality of PTT intervals based on the respective posture of the patient corresponding to the respective PTT interval, and monitoring, based on the classified plurality of PTT intervals, a patient condition.

In some examples, a non-transitory computer-readable medium includes instructions for causing one or more processors to collect, using a plurality of electrodes of a medical device, an electrogram (EGM) signal of a patient, wherein the EGM signal includes a plurality of depolarizations, collect, using an accelerometer of the medical device, an accelerometer signal that indicates which posture of a set of postures that the patient is occupying, collect, using a wearable device, a photoplethysmography (PPG) signal of the patient, wherein the PPG signal includes a plurality of PPG features indicating the occurrence of a cardiac pulse, determine, using processing circuitry in communication with a memory, a plurality of pulse transit time (PTT) intervals, wherein a PTT interval of the plurality of PTT intervals corresponds to each depolarization of the plurality of depolarizations, wherein each PTT interval of the plurality of PTT intervals represents an amount of time between the respective depolarization of the set of depolarizations and a PPG feature of the plurality of PPG features that occurs after the respective depolarization and before a subsequent depolarization of the plurality of depolarizations, determine, based on the accelerometer signal, a posture of the patient from a plurality of postures corresponding to each PTT interval of the plurality of PTT intervals, classify each PTT interval of the plurality of PTT intervals based on the respective posture of the patient corresponding to the respective PTT interval, and monitor, based on the classified plurality of PTT intervals, a patient condition.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIGS. 4A and 4B illustrate two additional example IMDs that may be substantially similar to the IMD of FIGS. 1-3, but which may include one or more additional features, in accordance with one or more techniques described herein.

Like reference characters denote like elements throughout the description and figures.

DETAILED DESCRIPTION

This disclosure describes techniques for measuring one or more pulse transit time (PTT) intervals in order to track one or more patient conditions. Changes in PTT may be a sign of a change (e.g., a worsening) of a patient condition such as hypertension. In some examples, it may be beneficial to track changes in PPT over a set of PTT intervals that are classified based on patient posture, patient motion level, and/or patient body angle. In this way, the medical device system described herein may analyze PTT intervals while controlling for a patient posture, a patient motion level, and/or a patient body angle associated in order to monitor a patient condition.

Figure 1:
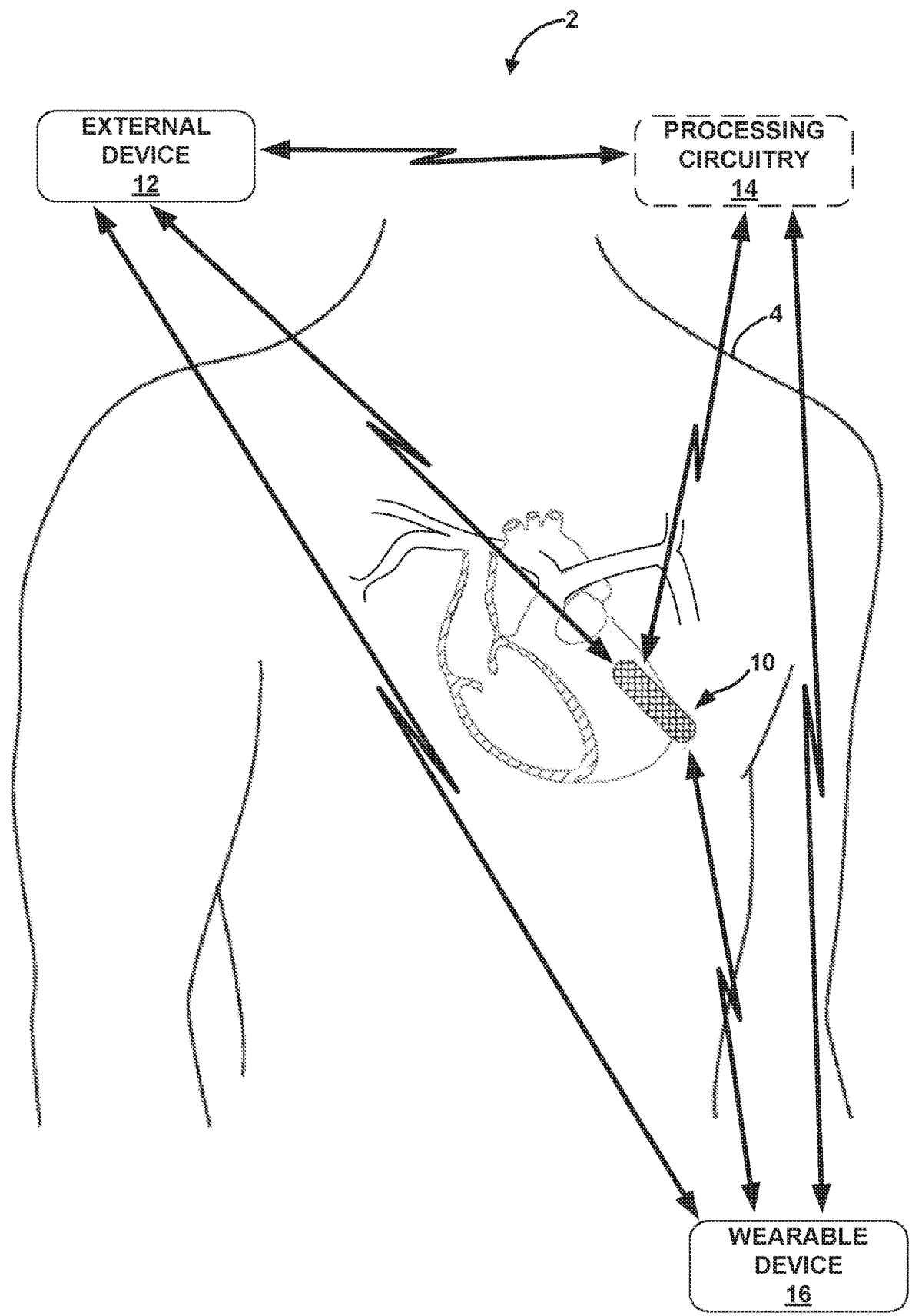
FIG. 1 illustrates the environment of an example medical device system in conjunction with a patient, in accordance with one or more techniques of this disclosure.

FIG. 1 illustrates the environment of an example medical device system 2 in conjunction with a patient 4, in accordance with one or more techniques of this disclosure. The example techniques may be used with an IMD 10, which may be in wireless communication with at least one of external device 12, processing circuitry 14, wearable device 16, and other devices not pictured in FIG. 1. For example, an external device (not pictured in FIG. 1) may include at least a portion of processing circuitry 14, the external device configured for communication with IMD 10, external device 12, and wearable device 16. In some examples, IMD 10 is implanted outside of a thoracic cavity of patient 4 (e.g., subcutaneously in the pectoral location illustrated in FIG. 1). IMD 10 may be positioned near the sternum near or just below the level of patient 4's heart, e.g., at least partially within the cardiac silhouette. In some examples, IMD 10 takes the form of a LINQ™ Insertable Cardiac Monitor (ICM), available from Medtronic plc, of Dublin, Ireland.

Clinicians sometimes diagnose patients with medical conditions based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patent is in a clinic for a medical appointment. However, in some examples, physiological markers (e.g., irregular heartbeats and long-term respiration trends) of a patient condition are rare or are difficult to observe over a relatively short period of time. As such, in these examples, a clinician may be unable to observe the physiological markers needed to diagnose a patient with a medical condition while monitoring one or more physiological signals of the patient during a medical appointment. In the example illustrated in FIG. 1, IMD 10 is implanted within patient 4 to continuously record one or more physiological signals of patient 4 over an extended period of time.

In some examples, IMD 10 includes a plurality of electrodes. The plurality of electrodes is configured to detect signals that enable processing circuitry of IMD 10 to determine current values of additional parameters associated with the cardiac and/or lung functions of patient 4. In some examples, the plurality of electrodes of IMD 10 are configured to detect a signal indicative of an electric potential of the tissue surrounding the IMD 10. Moreover, IMD 10 may additionally or alternatively include one or more optical sensors, accelerometers, temperature sensors, chemical sensors, light sensors, pressure sensors, in some examples. Such sensors may detect one or more physiological parameters indicative of a patient condition.

External device 12 may be a hand-held computing device with a display viewable by the user and an interface for providing input to external device 12 (i.e., a user input mechanism). For example, external device 12 may include a small display screen (e.g., a liquid crystal display (LCD) or a light emitting diode (LED) display) that presents information to the user. In addition, external device 12 may include a touch screen display, keypad, buttons, a peripheral pointing device, voice activation, or another input mechanism that allows the user to navigate through the user interface of external device 12 and provide input. If external device 12 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 12 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 12 is configured for use by the clinician, external device 12 may be used to transmit instructions to IMD 10. Example instructions may include requests to set electrode combinations for sensing and any other information that may be useful for programming into IMD 10. The clinician may also configure and store operational parameters for IMD 10 within IMD 10 with the aid of external device 12. In some examples, external device 12 assists the clinician in the configuration of IMD 10 by providing a system for identifying potentially beneficial operational parameter values.

Whether external device 12 is configured for clinician or patient use, external device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies). In some examples, external device 12 is configured to communicate with a computer network, such as the Medtronic CareLink® Network developed by Medtronic, plc, of Dublin, Ireland. For example, external device 12 may send data, such as data received from one or both of IMD 10 and wearable device 16, to another external device such as a smartphone, a tablet, or a desktop computer, and the other external device may in turn send the data to the computer network. In other examples, external device 12 may directly communicate with the computer network without an intermediary device.

Processing circuitry 14, in some examples, may include one or more processors that are configured to implement functionality and/or process instructions for execution within IMD 10. For example, processing circuitry 14 may be capable of processing instructions stored in a storage device. Processing circuitry 14 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 14 may include any suitable structure, whether in hardware, software, firmware, or any combination thereof, to perform the functions ascribed herein to processing circuitry 14.

Processing circuitry 14 may represent processing circuitry located within any one or combination of IMD 10, external device 12, and wearable device 16. In some examples, processing circuitry 14 may be entirely located within a housing of IMD 10. In other examples, processing circuitry 14 may be entirely located within a housing of external device 12. In other examples, processing circuitry 14 may be entirely located within a housing of wearable device 16. In other examples, processing circuitry 14 may be located within any combination of IMD 10, external device 12, wearable device 16, and another device or group of devices that are not illustrated in FIG. 1. As such, techniques and capabilities attributed herein to processing circuitry 14 may be attributed to any combination of IMD 10, external device 12, wearable device 16, and other devices that are not illustrated in FIG. 1.

Medical device system 2 of FIG. 1 is an example of a system for collecting an electrogram (EGM) signal according to one or more techniques of this disclosure. In some examples, processing circuitry 14 includes EGM analysis circuitry configured to determine one or more parameters of an EGM signal of patient 4. In one example, an EGM signal is sensed via one or more electrodes of IMD 10. An EGM is a signal representative of electrical activity of the heart, measured by electrodes implanted within the body, and often within the heart itself. For example, a cardiac EGM may include P-waves (depolarization of the atria), R-waves (depolarization of the ventricles), and T-waves (repolarization of the ventricles), among other events. Information relating to the aforementioned events, such as time separating one or more of the events, may be applied for a number of purposes, such as to determine whether an arrhythmia is occurring and/or predict whether an arrhythmia is likely to occur. Cardiac signal analysis circuitry, which may be implemented as part of processing circuitry 14, may perform signal processing techniques to extract information indicating the one or more parameters of the cardiac signal.

In some examples, IMD 10 includes one or more accelerometers. An accelerometer of IMD 10 may collect an accelerometer signal which reflects a measurement of any one or more of a motion of patient 4, a posture of patient 4 and a body angle of patient 4. In some cases, the accelerometer may collect a three-axis accelerometer signal indicative of patient 4's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 4 along a vertical axis, the lateral axis accelerometer signal vector may represent an acceleration of patient 4 along a lateral axis, and the frontal axis accelerometer signal vector may represent an acceleration of patient 4 along a frontal axis. In some cases, the vertical axis substantially extends along a torso of patient 4 when patient 4 from a neck of patient 4 to a waist of patient 4, the lateral axis extends across a chest of patient 4 perpendicular to the vertical axis, and the frontal axis extends outward from and through the chest of patient 4, the frontal axis being perpendicular to the vertical axis and the lateral axis.

Wearable device 16 may include a device that may be attached to the body of patient 4. In some examples, wearable device 16 may include a wearable wrist device such as a smart watch. In some examples, wearable device 16 may include a finger clip device for attaching wearable device 16 to a finger of patient 4. Wearable device 16 may include one or more optical sensors configured to generate a photoplethysmography (PPG) signal indicative of a perfusion of blood to the dermis and subcutaneous tissue of patient 4. In this way, the PPG signal may represent a pulse of patient 4, where the PPG signal rises during a pulse and falls during periods between pulses. The PPG signal may reflect each heartbeat of patient 4, a PPG peak corresponding to a heartbeat. In some examples, wearable device is located at an extremity (e.g., a finger, a wrist, a toe, or an ankle) of patient 4.

In some examples, processing circuitry 14 is configured to measure one or more PTT intervals. A PTT interval may represent an amount of time between a ventricular depolarization (e.g., R-wave or other EGM feature indicative of depolarization) of a heart of patient 4 and a subsequent peak or other feature of the PPG signal corresponding to the contraction resulting from the R-wave. For example, each peak of the PPG signal may represent a maximum blood perfusion level in tissue proximate to wearable device 16 during a respective heart cycle. During a heart cycle, the ventricles contract, causing blood to flow from the heart through the vasculature before returning to the heart via the atria. As such, a PTT interval may represent an amount of time that it takes for an example blood cell to flow from the ventricle of patient 4 to the tissue proximate to wearable device 16.

Although PTT intervals are described herein as being an amount of time between a ventricular depolarization of a heart of patient 4 and a subsequent peak of the PPG signal, processing circuitry 14 may define a PTT or another interval as having one or more different starting points and one or more different ending points. In some examples, the one or more starting points and the one or more ending points may include any combination of an atrial depolarization (e.g., a P-wave of the EGM signal), a repolarization of the ventricles (e.g., a T-wave of the EGM signal), a PPG signal valley, and a PPG signal inflection point). For example, processing circuitry 14 may measure an interval between a P-wave of the EGM signal and a PPG valley of the PPG signal, where the PPG valley corresponds to the same heartbeat (e.g., heart cycle) as the P-wave.

Processing circuitry 14 may determine a PTT interval relating to at least one R-wave of the plurality of R-waves in the EGM signal collected by IMD 10. For example, processing circuitry 14 may determine an amount of time between the at least one R-wave of the plurality of R-waves and a respective PPG feature of a plurality of PPG features that occurs after the respective R-wave. In some cases, the respective PPG feature occurs due to a ventricular depolarization denoted by an R-wave in the EGM signal. In some such cases, the PPG feature may represent a PPG "peak." In some examples, a PPG feature that is recorded due to a ventricular depolarization marked by a first R-wave may occur before a second R-wave that is subsequent to the first R-wave, where the second R-wave is consecutive to the first R-wave.

One way that processing circuitry 14 may detect peaks in the EGM signal and the PPG signal is for processing circuitry 14 to calculate a derivative (e.g., difference) of the respective signal and identify one or more "zero crossings" of the signal. For example, to calculate one or more PPG peaks in the PPG signal, processing circuitry 14 may calculate a derivative of the PPG signal. Subsequently, in some cases, processing circuitry 14 is configured to identify a set of positive-going-negative zero crossings and a set of negative-going-positive zero crossings in the derivative of the PPG signals. The set of positive-going-negative zero crossings may represent relative peaks of the PPG signal, since a positive-going-negative zero crossing in the derivative of the PPG signal represents a point in which a slope of the PPG signal changes from being a positive slope to being a negative slope. The set of negative-going-positive zero crossings may represent relative valleys of the PPG signal, since a negative-going-positive zero crossing in the derivative of the PPG signal represents a point in which a slope of the PPG signal changes from being a negative slope to being a positive slope.

In some examples, to identify the one or more PPG peaks in the PPG signal, processing circuitry 14 may implement a "blanking window" following each detected PPG signal of the one or more PPG signals. For example, processing circuitry 14 may start a blanking window following a detected PPG peak in order to cause processing circuitry 14 to disregard any positive-going-negative zero crossings in the PPG signal which occur during the blanking window which extends for a period of time after the detected PPG peak. In some examples, processing circuitry 14 sets the length of the blanking window based on a heart rate of patient 4. For example, processing circuitry 14 may set the blanking window to a first length if patient 4 has a first hear rate and processing circuitry 14 may set the blanking window to a second length if patient 4 has a second heart rate, where the first blanking window is longer than the second blanking window if the first heart rate is lower than the second heart rate, and where the first blanking window is shorter than the second blanking window if the first heart rate is higher than the second heart rate. In some examples, processing circuitry 14 only detects one PPG peak per heart cycle, and the blanking window may prevent processing circuitry 14 from detecting more than one PPG peak per heart cycle.

PTT intervals can vary based on one or more factors relating to patient 4 such as one or more of a posture of patient 4, a motion level of patient 4, a body angle of patient 4, and a heart rate of patient 4. It may be beneficial to analyze a set of PTT intervals that are collected while posture and/or body angle is held constant. Consequently, when processing circuitry 144 measures a plurality of PTT intervals, it may be beneficial for processing circuitry 14 to classify the PTT intervals based on the one or more factors relating to patient 4. For example, processing circuitry 14 may determine, based on the accelerometer signal collected by IMD 10, a posture of patient 4 during a period of time in which IMD 10 collects the portion of the EGM signal that processing circuitry 14 analyzes for the PTT interval. The accelerometer signal may indicate which posture of a set of postures patient 4 is occupying, such as supine, prone, lying on a left side, lying on a right side, sitting, and standing. In some examples, processing circuitry 14 may determine a body angle value of patient 4 based on the accelerometer signal which represents an angle of the body of patient 4 relative to the ground. Processing circuitry 14 classify each PTT interval of the plurality of PTT intervals based on one or more of a posture of patient 4, a body angle of patient 4, and a motion level of patient 4.

In some examples, it may be beneficial for processing circuitry 14 to analyze a set of PTT intervals that are collected while a motion level of patient 4 is lower than a threshold motion level. Processing circuitry 14 may determine a motion level of patient 4 based on the accelerometer signal. For example, processing circuitry 14 may calculate an activity count value using the accelerometer signal, where the activity count value represents the motion level of the patient. In some examples, processing circuitry 14 may classify each PTT interval as being measured using data that is collected while the motion level is greater than equal to the threshold motion level or as being performed using data that is collected while the motion level is less than the threshold motion level.

In some examples, processing circuitry 14 may monitor, based on the classified plurality of PTT intervals, a patient condition. In some examples, to monitor the patient condition, processing circuitry 14 is configured to calculate, based on information identifying each PTT interval of the plurality of PTT intervals with the determined posture of the patient, a median of a set of PTT intervals which occur over a period of time preceding a present time. Each PTT interval of the set of PTT intervals may be classified as corresponding to a first group of postures of the plurality of postures. In this way, in monitoring the patient condition, processing circuitry 14 may only analyze PTT intervals which occur while patient 4 is in a specific one or more postures. For example, processing circuitry 14 may determine, based on the median of the set of PTT intervals, a trend. Processing circuitry 14 may calculate a set of PTT median values, wherein each PTT median value of the set of PTT median values is a median of a respective set of PTT intervals occurring over a respective period of time. To calculate the trend, processing circuitry 14 may determine whether the set of PTT median values represent a change in PTT interval length. In some cases, based on the identified trend, processing circuitry may determine a therapy to be delivered to patient 4, and/or output an alert prompting patient 4 to seek medical attention.

Although in one example IMD 10 takes the form of an ICM, in other examples, IMD 10 takes the form of any combination of implantable cardioverter defibrillators (ICDs) with intravascular or extravascular leads, pacemakers, cardiac resynchronization therapy devices (CRT-Ds), neuromodulation devices, left ventricular assist devices (LVADs), implantable sensors, orthopedic devices, or drug pumps, as examples. Moreover, techniques of this disclosure may be used to measure one or more PTT intervals based on an EGM signal and/or an accelerometer signal collected by one or more of the aforementioned devices.

Figure 2:
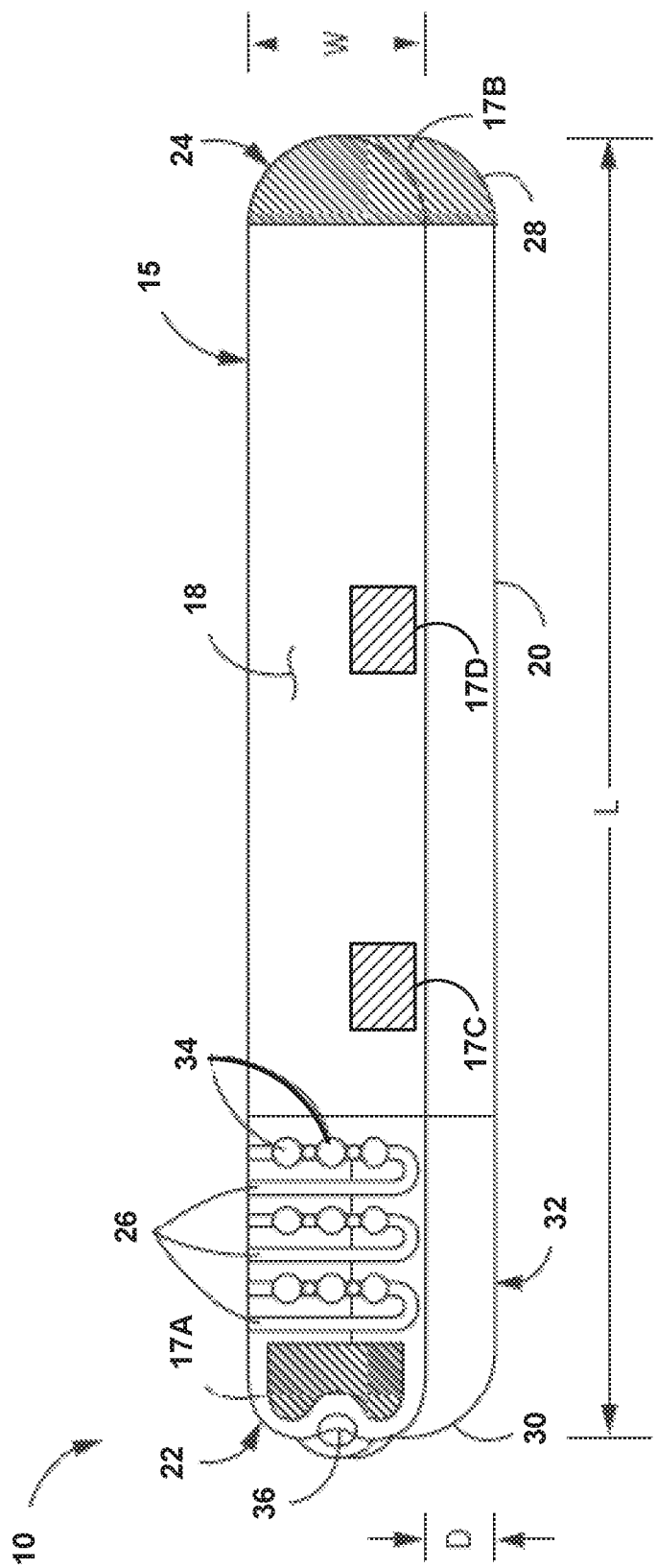
FIG. 2 is a conceptual drawing illustrating an example configuration of an implantable medical device (IMD) of the medical device system of FIG. 1, in accordance with one or more techniques described herein.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 17A, and distal electrode 17B. Housing 15 may further include first major surface 18, second major surface 20, proximal end 22, and distal end 24. In some examples, IMD 10 may include one or more additional electrodes 17C, 17D positioned on one or both of major surfaces 18,20 of IMD 10. Housing 15 encloses electronic circuitry located inside the IMD 10, and protects the circuitry contained therein from fluids such as body fluids. In some examples, electrical feedthroughs provide electrical connection of electrodes 17A-17D, and antenna 26, to circuitry within housing 15. In some examples, electrode 17B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 17A and distal electrode 17B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4.

In the example shown in FIG. 2, first major surface 18 of IMD 10 faces outward towards the skin, when IMD 10 is inserted within patient 4, whereas second major surface 20 is faces inward toward musculature of patient 4. Thus, first and second major surfaces 18,20 may face in directions along a sagittal axis of patient 4 (see FIG. 1), and this orientation may be maintained upon implantation due to the dimensions of IMD 10.

Proximal electrode 17A and distal electrode 17B may be used to sense cardiac EGM signals (e.g., ECG signals) when IMD 10 is implanted subcutaneously in patient 4. In some examples, processing circuitry of IMD 10 also may determine one or more PTT intervals based on the cardiac EGM signals, which processing circuitry 14 may evaluate in determining whether a medical condition (e.g., heart failure) of patient 4 has changed. The cardiac ECG signals may be stored in a memory of the IMD 10, and data derived from the cardiac ECG signals may be transmitted via integrated antenna 26 to another medical device, such as external device 12. In some examples, one or both of electrodes 17A and 17B also may be used by IMD 10 to detect impedance values during impedance measurements performed by IMD 10. In some examples, such impedance values detected by IMD 10 may reflect a resistance value associated with a contact between electrodes 17A, 17B, and target tissue of patient 4. Additionally, in some examples, electrodes 17A, 17B may be used by communication circuitry of IMD 10 for tissue conductance communication (TCC) communication with external device 12 or another device.

In the example shown in FIG. 2, proximal electrode 17A is in close proximity to proximal end 22, and distal electrode 17B is in close proximity to distal end 24 of IMD 10. In this example, distal electrode 17B is not limited to a flattened, outward facing surface, but may extend from first major surface 18, around rounded edges 28 or end surface 30, and onto the second major surface 20 in a three-dimensional curved configuration. As illustrated, proximal electrode 17A is located on first major surface 18 and is substantially flat and outward facing. However, in other examples not shown here, proximal electrode 17A and distal electrode 17B both may be configured like proximal electrode 17A shown in FIG. 2, or both may be configured like distal electrode 17B shown in FIG. 2. In some examples, additional electrodes 17C and 17D may be positioned on one or both of first major surface 18 and second major surface 20, such that a total of four electrodes are included on IMD 10. Any of electrodes 17A-17D may be formed of a biocompatible conductive material. For example, any of electrodes 17A-17D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 17A, integrated antenna 26, anti-migration projections 34, and suture hole 36. Integrated antenna 26 is located on the same major surface (e.g., first major surface 18) as proximal electrode 17A, and may be an integral part of header assembly 32. In other examples, integrated antenna 26 may be formed on the major surface opposite from proximal electrode 17A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, WiFi®, or other proprietary or non-proprietary wireless telemetry communication schemes. Antenna 26 may be coupled to communication circuitry of IMD 10, which may drive antenna 26 to transmit signals to external device 12, and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 15 may include anti-migration projections 34 positioned adjacent integrated antenna 26. Anti-migration projections 34 may include a plurality of bumps or protrusions extending away from first major surface 18, and may help prevent longitudinal movement of IMD 10 after implantation in patient 4. In other examples, anti-migration projections 34 may be located on the opposite major surface as proximal electrode 17A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 17A. In some examples, header assembly 32 may include a molded header assembly made from a polymeric or plastic material, which may be integrated or separable from the main portion of IMD 10.

Electrodes 17A and 17B may be used to sense cardiac ECG signals, as described above. Additional electrodes 17C and 17D may be used to sense subcutaneous tissue impedance, in addition to or instead of electrodes 17A, 17B, in some examples. In some examples, processing circuitry of IMD 10 may determine an impedance value of patient 4 based on signals received from at least two of electrodes 17A-17D. For example, processing circuitry of IMD 10 may generate one of a current or voltage signal, deliver the signal via a selected two or more of electrodes 17A-17D, and measure the resulting other of current or voltage. Processing circuitry of IMD 10 may determine an impedance value based on the delivered current or voltage and the measured voltage or current.

In some examples, IMD 10 may include one or more additional sensors, such as one or more accelerometers (not shown). Such accelerometers may be 3D accelerometers configured to generate signals indicative of one or more types of movement of the patient, such as gross body movement (e.g., motion) of the patient, patient posture, movements associated with the beating of the heart, or coughing, rales, or other respiration abnormalities. One or more of the parameters monitored by IMD 10 (e.g., impedance, EGM) may fluctuate in response to changes in one or more such types of movement. For example, changes in parameter values sometimes may be attributable to increased patient motion (e.g., exercise or other physical motion as compared to immobility) or to changes in patient posture, and not necessarily to changes in a medical condition. Thus, in some methods of identifying or tracking a medical condition of patient 4, it may be advantageous to account for such fluctuations when determining whether a change in a parameter is indicative of a change in a medical condition.

Figure 3:
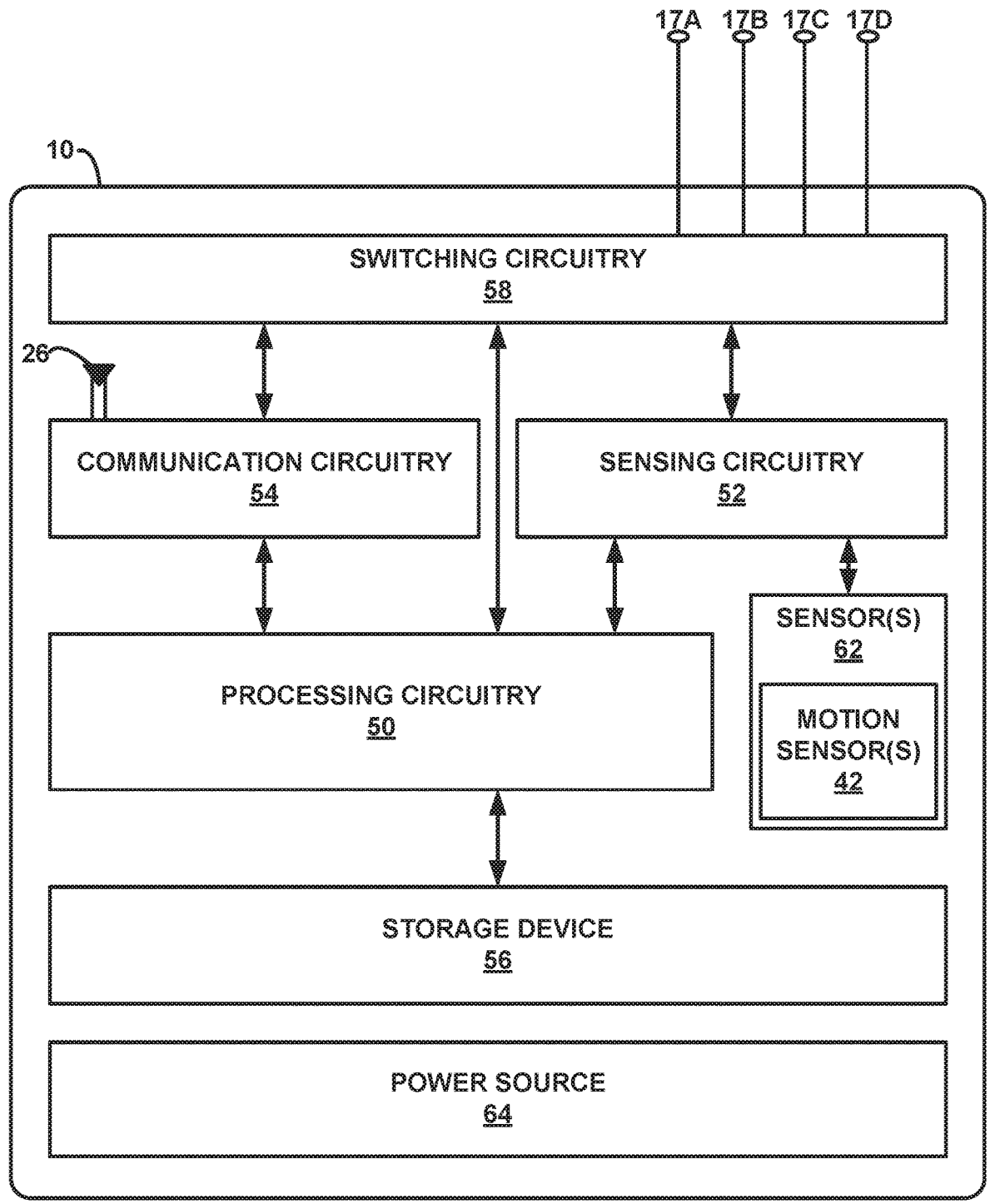
FIG. 3 is a functional block diagram illustrating an example configuration of the IMD of FIGS. 1 and 2, in accordance with one or more techniques described herein.

FIG. 3 is a functional block diagram illustrating an example configuration of IMD 10 of FIGS. 1 and 2, in accordance with one or more techniques described herein. In the illustrated example, IMD 10 includes electrodes 17, antenna 26, processing circuitry 50, sensing circuitry 52, communication circuitry 54, storage device 56, switching circuitry 58, sensors 62 including motion sensor(s) 42, and power source 64.

Processing circuitry 50 may include fixed function circuitry and/or programmable processing circuitry. Processing circuitry 50 may include any one or more of a microprocessor, a controller, a DSP, an ASIC, an FPGA, or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof. Processing circuitry 14 (FIG. 1) may be, or may include, processing circuitry 50 of IMD 10.

Sensing circuitry 52 and communication circuitry 54 may be selectively coupled to electrodes 17A-17D via switching circuitry 58, as controlled by processing circuitry 50. Sensing circuitry 52 may monitor signals from electrodes 17A-17D in order to monitor electrical activity of heart (e.g., to produce an ECG). Sensing circuitry 52 also may monitor signals from sensors 62, which may include motion sensor(s) 42, and any additional light detectors that may be positioned on IMD 10. In some examples, sensing circuitry 52 may include one or more filters and amplifiers for filtering and amplifying signals received from one or more of electrodes 17A-17D and/or motion sensor(s) 42.

In some examples, sensing circuitry 52 may include circuitry configured to detect one or more features (R-waves, P-waves, and T-waves) of the EGM signal collected by IMD 10. For example, sensing circuitry may include one or more amplifiers and one or more electronic filters configured to detect an occurrence of each R-wave of the EGM signal and generate an indication of a time in which each R-wave of the EGM signal is collected by IMD 10. In turn, processing circuitry 50 may store data indicative of the occurrence of each R-wave and the time of each R-wave in storage device 56. In this way, the time of each R-wave of the R-waves included in the EGM signals may be used to determine one or more PTT intervals.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, wearable device 16, or by using another local or networked computing device configured to communicate with processing circuitry 50 via communication circuitry 54. The clinician may also program parameters of IMD 10 using external device 12, wearable device 16 or another local or networked computing device.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Power source 64 is configured to deliver operating power to the components of IMD 10. Power source 64 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 64 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 4A:
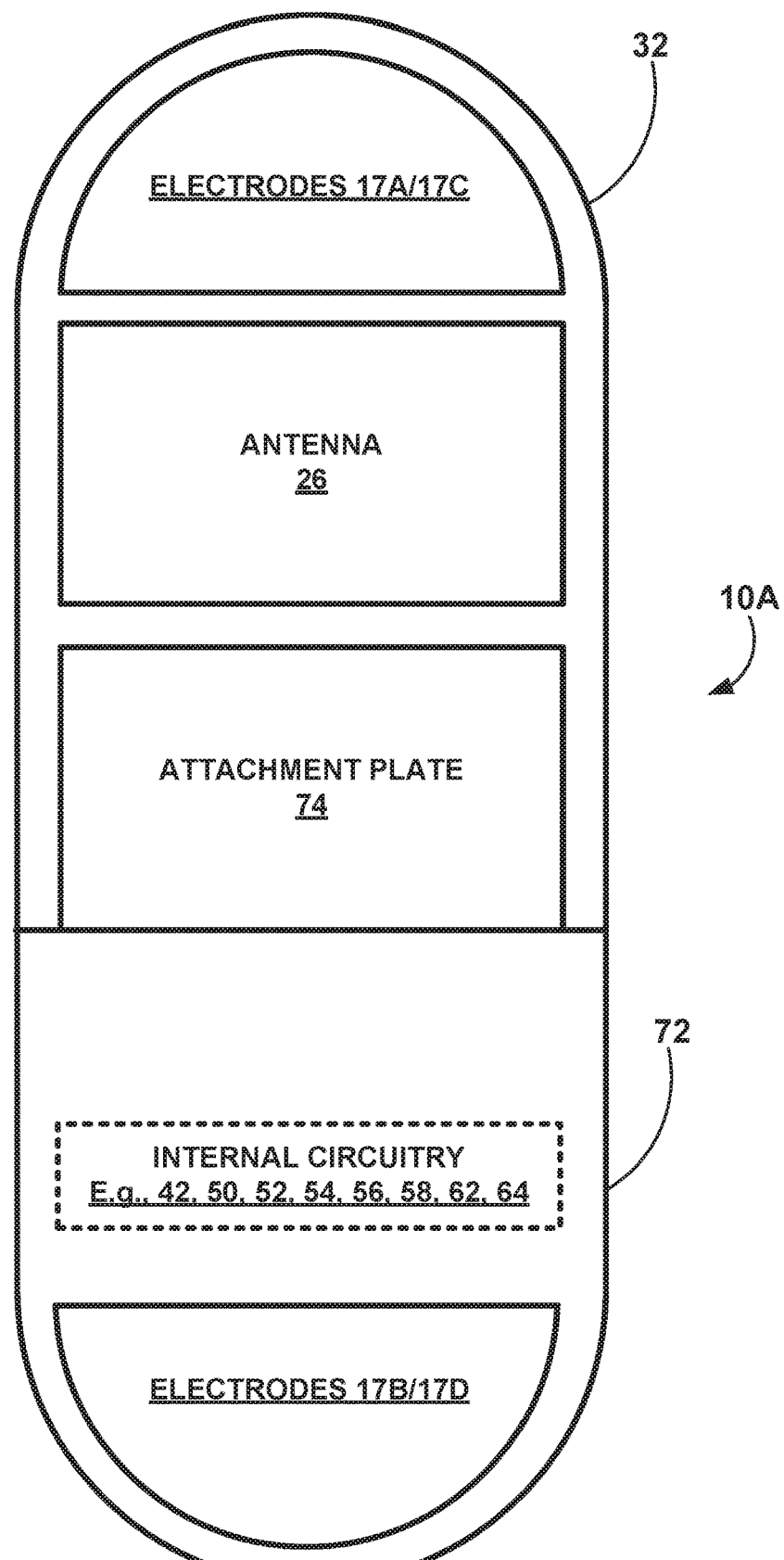

FIGS. 4A and 4B illustrate two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, storage device 56, switching circuitry 58, internal components of sensors 62, and power source 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 17A-17D on housing 15B and processing circuitry 50. In some examples, insulative cover 76 may be positioned over an open housing 15 to form the housing for the components of IMD 10B. One or more components of IMD 10B (e.g., antenna 26, processing circuitry 50, sensing circuitry 52, communication circuitry 54, switching circuitry 58, and/or power source 64) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Insulative cover 76 may be configured so as not to interfere with the operation of IMD 10B. For example, one or more of electrodes 17A-17D may be formed or placed above or on top of insulative cover 76, and electrically connected to switching circuitry 58 through one or more vias (not shown) formed through insulative cover 76. Insulative cover 76 may be formed of sapphire (i.e., corundum), glass, parylene, and/or any other suitable insulating material. In some examples, insulative cover 76 may have a thickness of about 300 micrometers to about 600 micrometers. Housing 15B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
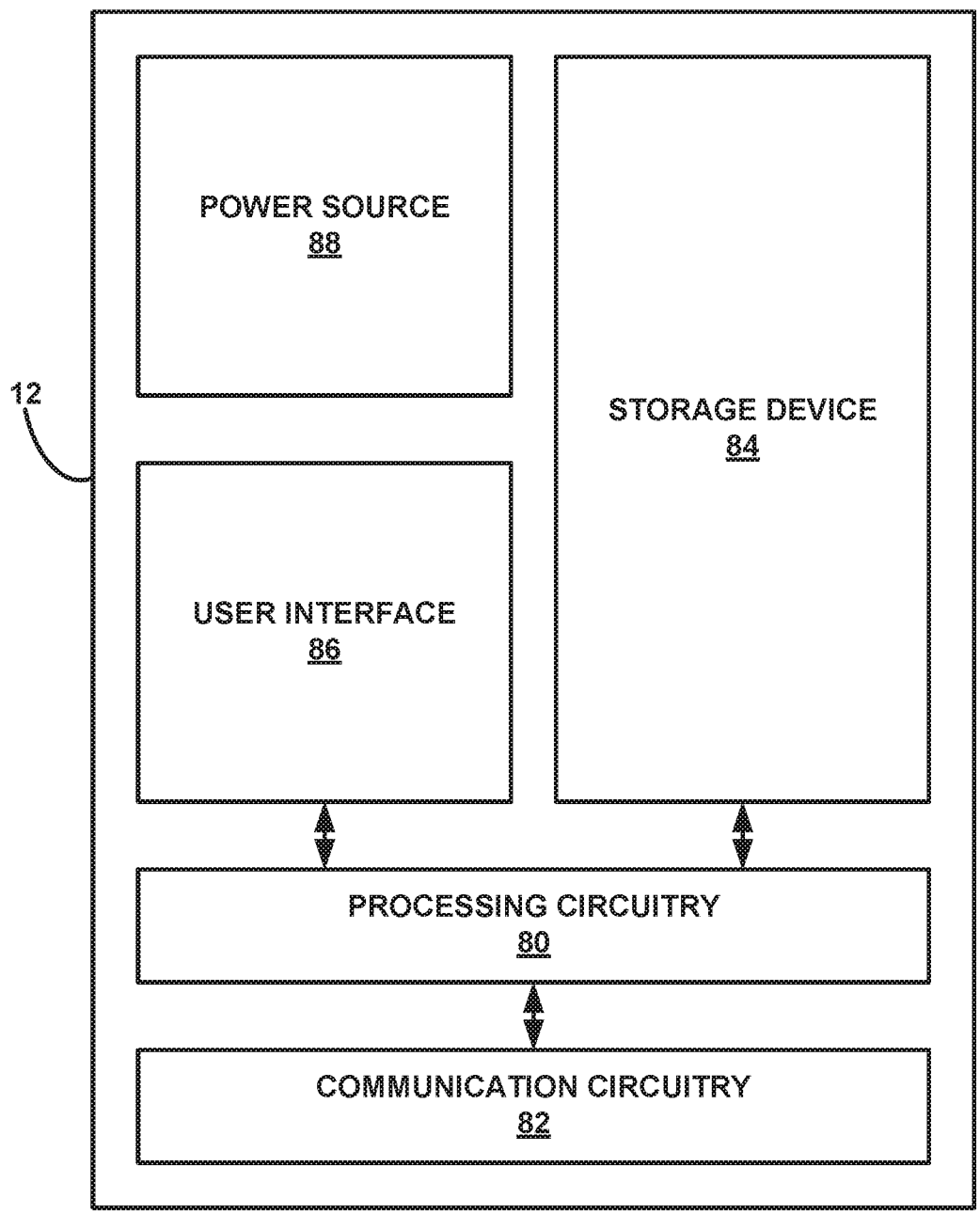
FIG. 5 is a block diagram illustrating an example configuration of components of an external device, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, storage device 84, user interface 86, and power source 88.

Processing circuitry 80, in one example, may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as one or both of IMD 10 and wearable device 16. Under the control of processing circuitry 80, communication circuitry 82 may receive downlink telemetry from, as well as send uplink telemetry to, IMD 10, wearable device 16, or another device.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, dynamic random access memories (DRAM), static random access memories (SRAM), magnetic discs, optical discs, flash memories, or forms of electrically programmable memories (EPROM) or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data corresponding to one or both of an ECG signal and an accelerometer signal) to external device 12. In turn, external device 12 may receive the collected data from IMD 10 and store the collected data in storage device 84. Additionally, or alternatively, processing circuitry 80 may export instructions to IMD 10 requesting IMD 10 to update electrode combinations for stimulation or sensing. In some examples, processing circuitry 80 may transmit an instruction to wearable device 16 which requests wearable device 16 to export collected data (e.g., data corresponding to a PPG signal) to external device 12. In turn, external device 12 may receive the collected data from wearable device 16 and store the collected data in storage device 84.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
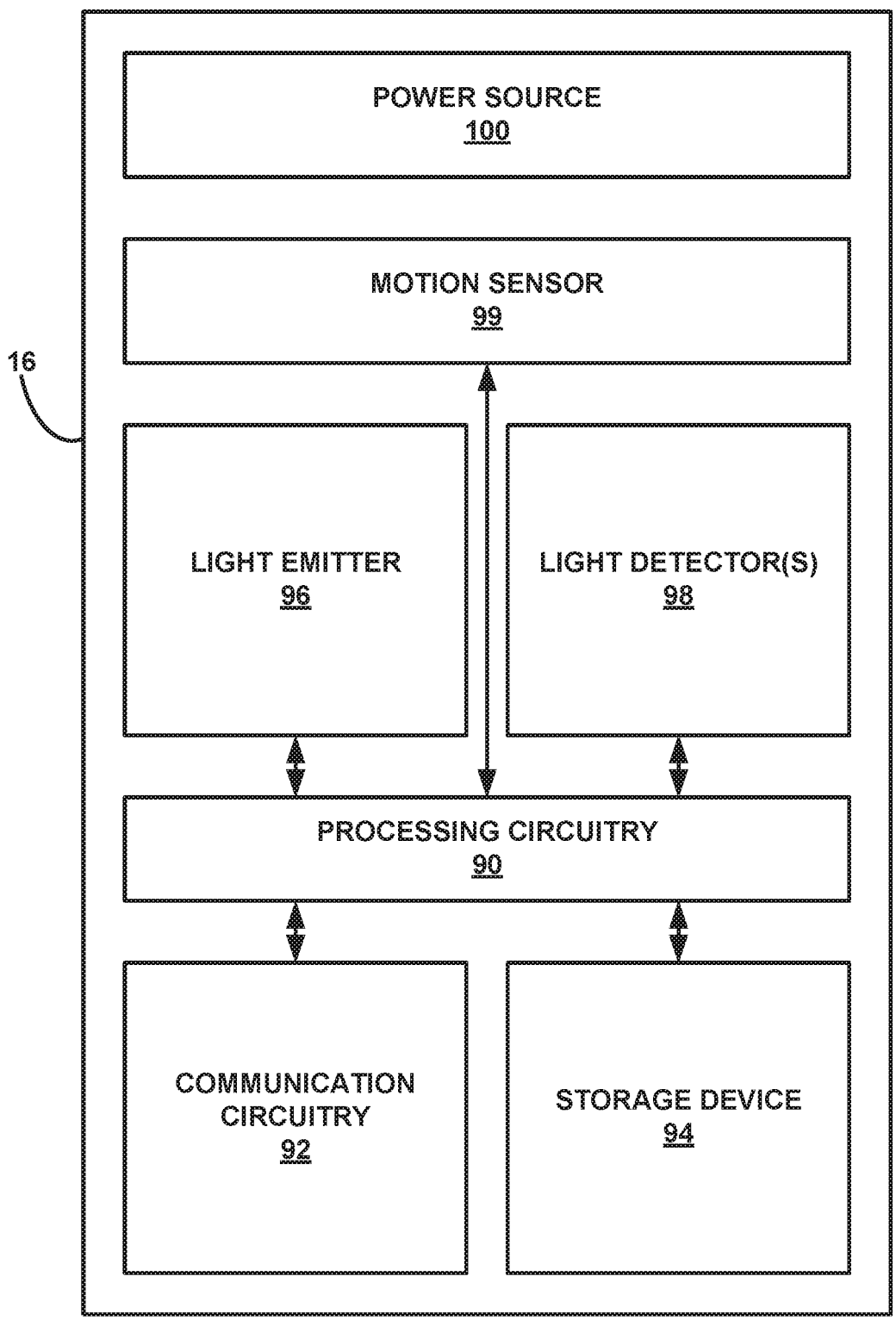
FIG. 6 is a block diagram illustrating an example configuration of components of a wearable device, in accordance with one or more techniques of this disclosure.

FIG. 6 is a block diagram illustrating an example configuration of components of wearable device 16, in accordance with one or more techniques of this disclosure. In the example of FIG. 5, wearable device 16 includes processing circuitry 90, communication circuitry 92, storage device 94, light emitter 96, light detector(s) 98, and power source 100.

Processing circuitry 80, in one example, may include one or more processors that are configured to implement functionality and/or process instructions for execution within wearable device 16. For example, processing circuitry 90 may be capable of processing instructions stored in storage device 94. Processing circuitry 90 may include, for example, microprocessors, DSPs, ASICs, FPGAs, or equivalent discrete or integrated logic circuitry, or a combination of any of the foregoing devices or circuitry. Accordingly, processing circuitry 90 may include any suitable structure, whether in hardware, software, firmware, or any combination thereof, to perform the functions ascribed herein to processing circuitry 90.

Communication circuitry 92 may include any suitable hardware, firmware, software or any combination thereof for communicating with another device, such as one or both of IMD 10 and external device 12. Under the control of processing circuitry 90, communication circuitry 92 may receive downlink telemetry from, as well as send uplink telemetry to, IMD 10, external device 12, or another device.

Storage device 94 may be configured to store information within wearable device 16 during operation. Storage device 94 may include a computer-readable storage medium or computer-readable storage device. In some examples, storage device 94 includes one or more of a short-term memory or a long-term memory. Storage device 94 may include, for example, RAM, DRAM, SRAM, magnetic discs, optical discs, flash memories, or forms of EPROM or EEPROM. In some examples, storage device 94 is used to store data indicative of instructions for execution by processing circuitry 90. Storage device 94 may be used by software or applications running on wearable device 16 to temporarily store information during program execution.

Wearable device 16 may include light emitter 96 and light detector(s) 98 configured to perform one or more PPG measurements. Light emitter 96 may include one or more light emitting elements (e.g., LEDs). To perform a PPG measurement, light emitter 96 may illuminate tissue of patient 4 proximate to wearable device 16. Light detector(s) 98 may collect a PPG signal which indicates an amount of light absorbed by the tissue proximate to wearable device 16. In other words, light detector(s) 98 may detect at least some photons emitted by light emitter 96 and reflected by the tissue proximate to light emitter 96. An amount of light from light emitter 96 that is detected by light detector(s) 98 may be inversely proportional to an amount of light from light emitter 96 that is absorbed by the tissue of patient 4. The amount of light absorbed by the tissue may be correlated with a volume of blood present in the tissue proximate to wearable device 16. In this way, the PPG signal may include information indicative of one or more heart cycles of patient 4.

For example, each heart cycle of patient 4 may include a period of time in which a volume of blood in peripheral vasculature of patient 4 is elevated as compared with the rest of the heart cycle. Such a period of time may represent a PPG peak. The PPG data collected by light detector(s) 98 may include a PPG peak corresponding to each heart cycle which occurs during a PPG measurement performed by wearable device 16.

In some examples, wearable device 16 may include motion sensor 99 (e.g., an accelerometer) configured to measure a motion level of patient 4 at a location (e.g., an extremity such as a wrist, a finger, an ankle, or a toe) in which wearable device 16 is worn. For example, if wearable device 16 is worn on a wrist of patient 4, motion sensor 99 may generate a signal indicating a motion level of the wrist of patient 4. Additionally, in some cases, if wearable device 16 is worn on a finger of patient 4, motion sensor 99 may generate a signal indicating a motion level of the wrist of patient 4. In some examples, processing circuitry (e.g., processing circuitry 14) may receive information indicative of a motion level of the extremity that wearable device 16 is worn on for each heart cycle of a plurality of heart cycles identifiable in the PPG signal collected by light detector(s) 98 of wearable device 16. In this way, processing circuitry 14 may select heart cycles for PTT measurements based on whether the extremity in which wearable device 16 is worn is active. For example, processing circuitry 14 may select one or more heart cycles for PTT analysis, wherein each heart cycle of the one or more heart cycles occur when a motion level of the extremity in which wearable device 16 is worn is below a threshold motion level. In some examples, processing circuitry 14 may decline to perform PTT analysis of the PPG data and/or the ECG data based on an activity level of the extremity, as measured by motion sensor 99.

It may be beneficial for processing circuitry 14 to analyze PTT intervals in which patent 4 is in a particular body position. For example, processing circuitry 14 may perform PTT analysis corresponding to one or more heart cycles in which patient 4 is sitting with arms still. The motion sensors of IMD 10 may indicate whether patient 4 is sitting and motion sensor 99 of wearable device 16 may indicate whether an arm of patient 4 is still. As such processing circuitry 14 may identify periods of overlap between when patient 4 is sitting and when the arm of patient 4 is still, and processing circuitry 14 may perform PTT analysis using portions of the EGM signal and the PPG signal that are collected during such periods of overlap. In some examples, processing circuitry 14 may perform PTT analysis using portions of the EGM signal and the PPG signal that are collected after patient 4 has been in a particular position (e.g., sitting with arms still) for longer than a threshold amount of time. In some examples, processing circuitry 14 may output, via an application, a message to wearable device 16 or another device such as external device 12 or a smart device. The message may instruct patient 14 to enter a specific body position (e.g., sitting with arms still, lying down with arms still, or standing with arms still). Subsequently, processing circuitry 14 may perform PTT analysis on a portion of the EGM signal and the PPG signal that occurs after the instruction to enter the specific body position.

Power source 100 is configured to deliver operating power to the components of wearable device 16. Power source 100 may include a battery and a power generation circuit to produce the operating power. In some examples, the battery is rechargeable to allow extended operation. Recharging may be accomplished by electrically coupling power source 100 to a cradle or plug that is connected to an AC outlet. In addition, recharging may be accomplished through proximal inductive interaction between an external charger and an inductive charging coil within wearable device 16. In other examples, traditional batteries (e.g., nickel cadmium or lithium ion batteries) may be used. In addition, wearable device 16 may be directly coupled to an alternating current outlet to operate.

Figure 7:
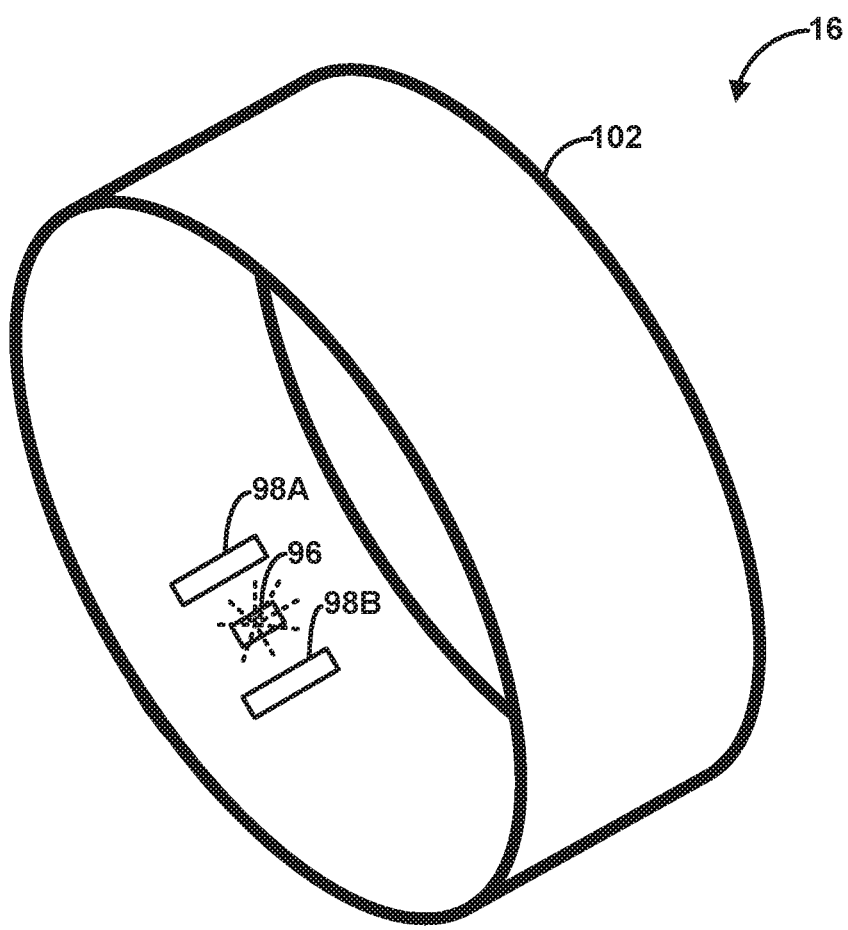
FIG. 7 is a conceptual drawing illustrating an example configuration of the wearable device of the medical device system of FIG. 1, in accordance with one or more techniques described herein.

FIG. 7 is a conceptual drawing illustrating an example configuration of wearable device 16 of the medical device system 2 of FIG. 1, in accordance with one or more techniques described herein. As seen in FIG. 7, wearable device 16 may include a band 102. Light emitter 96 and light detectors 98A and 98B (hereinafter, "light detectors 98") may be located on an interior surface of band 102 such that light emitter 96 and light detectors 98 face tissue of patient 4 when wearable device 16 is worn by patient 4. The example configuration of wearable device 16 illustrated in FIG. 7 may represent a ring for placement on a finger of patient 4. In other examples not illustrated in FIG. 7, wearable device 16 may include another device configured to be attached to the body of patient 4 such as a wrist bracelet, an ankle bracelet, a finger clip, or a smart device such as a smart watch. In any case, wearable device 16 may include light emitter 96 and light detectors 98 such that light emitter 96 and light detectors 98 may produce a PPG signal including one or more PPG peaks or other features corresponding to pulses of respective heart cycles.

Figure 8:
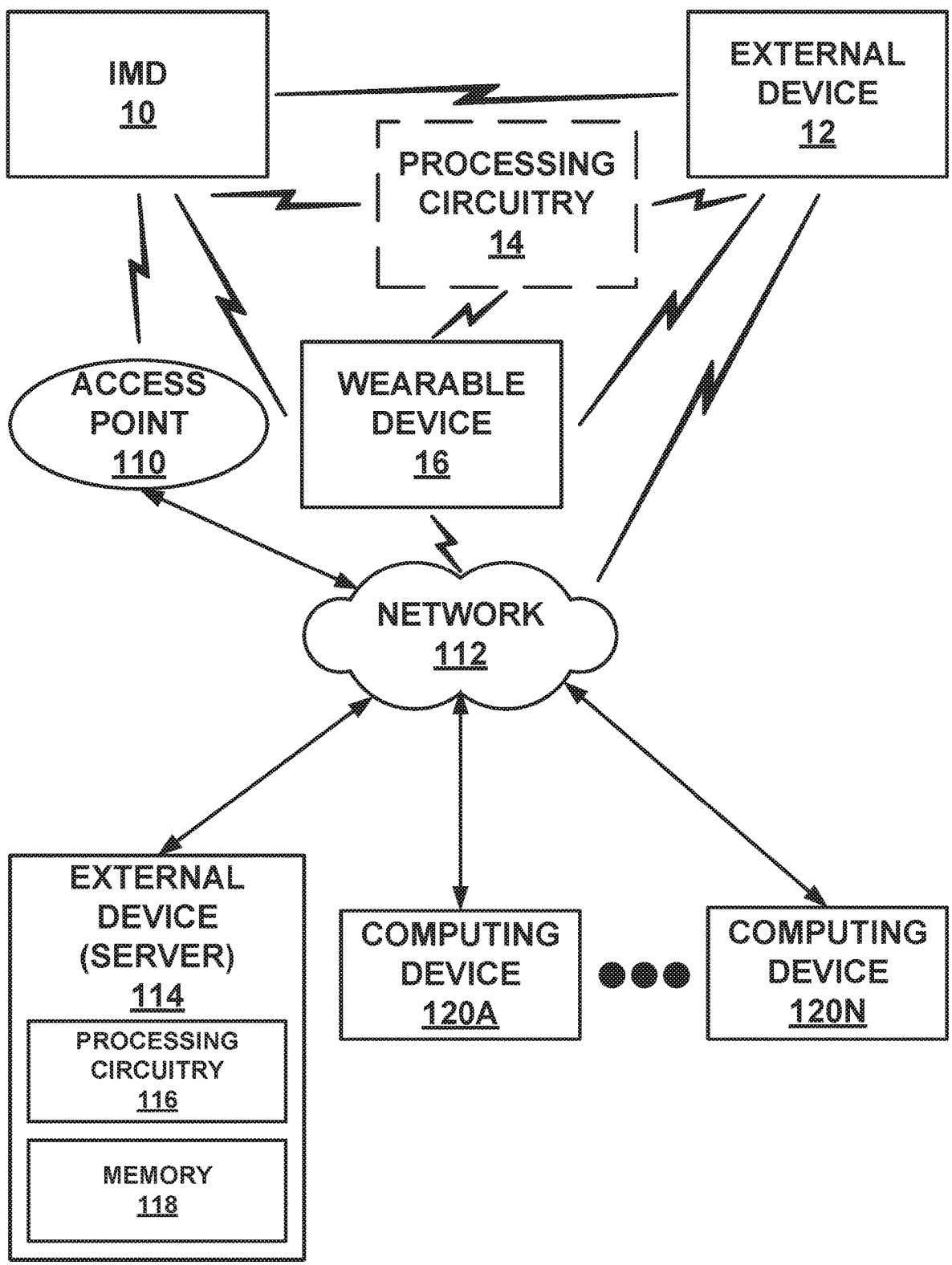
FIG. 8 is a block diagram illustrating an example system that includes an access point, a network, external computing devices, such as a server, and one or more other computing devices, which may be coupled to an IMD, an external device, processing circuitry, and a wearable device via a network, in accordance with one or more techniques described herein.

FIG. 8 is a block diagram illustrating an example system that includes an access point 110, a network 112, external computing devices, such as a server 114, and one or more other computing devices 120A-120N, which may be coupled to IMD 10, external device 12, processing circuitry 14, and wearable device 16 via network 112, in accordance with one or more techniques described herein. In this example, IMD 10 may use communication circuitry 54 to communicate with external device 12 via a first wireless connection, to communicate with an access point 110 via a second wireless connection, and to communicate with wearable device 16 via a third wireless connection. In the example of FIG. 8, access point 110, external device 12, wearable device 16, server 114, and computing devices 120A-120N are interconnected and may communicate with each other through network 112.

Access point 110 may include a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be a user device, such as a tablet or smartphone, that may be co-located with the patient. As discussed above, IMD 10 may be configured to transmit data, such as any one or both of an EGM signal and an accelerometer signal, or data derived from the EGM and accelerometer signals, such as data indicating the timing of R-waves, activities, and postures. In addition, access point 110 may interrogate IMD 10, such as periodically or in response to a command from the patient or network 112, in order to retrieve such signals or data, parameter values determined by processing circuitry 50 of IMD 10, or other operational or patient data from IMD 10. Access point 110 may then communicate the retrieved data to server 114 via network 112.

In some cases, server 114 may be configured to provide a secure storage site for data that has been collected from IMD 10, external device 12, and/or wearable device 16. In some cases, server 114 may assemble data in web pages or other documents for viewing by trained professionals, such as clinicians, via computing devices 120A-120N. One or more aspects of the illustrated system of FIG. 8 may be implemented with general network technology and functionality, which may be similar to that provided by the Medtronic CareLink® Network developed by Medtronic plc, of Dublin, Ireland.

Server 114 may include processing circuitry 116. Processing circuitry 116 may include fixed function circuitry and/or programmable processing circuitry. Processing circuitry 116 may include any one or more of a microprocessor, a controller, a DSP, an ASIC, an FPGA, or equivalent discrete or analog logic circuitry. In some examples, processing circuitry 116 may include multiple components, such as any combination of one or more microprocessors, one or more controllers, one or more DSPs, one or more ASICs, or one or more FPGAs, as well as other discrete or integrated logic circuitry. The functions attributed to processing circuitry 116 herein may be embodied as software, firmware, hardware or any combination thereof. In some examples, processing circuitry 116 may perform one or more techniques described herein based on an EGM signal and/or an accelerometer signal, or data derived from these signals, received from IMD 10, or based on a PPG signal, or data derived from the PPG signal, received from wearable device 16, as examples.

Server 114 may include memory 118. Memory 118 includes computer-readable instructions that, when executed by processing circuitry 116, cause processing circuitry 116 to perform various functions attributed to server 114 and processing circuitry 116 herein. Memory 118 may include any volatile, non-volatile, magnetic, optical, or electrical media, such as RAM, ROM, NVRAM, EEPROM, flash memory, or any other digital media.

In some examples, one or more of computing devices 120A-120N (e.g., device 120A) may be a tablet or other smart device located with a clinician, by which the clinician may program, receive alerts from, and/or interrogate one or both of IMD 10 and wearable device 16. For example, the clinician may access data corresponding to an EGM signal and/or an accelerometer signal collected by IMD 10 through device 120A, such as when patient 4 is in between clinician visits, to check on a status of a medical condition. Additionally, or alternatively, the clinician may access data corresponding to a PPG signal collected by wearable device 16 through device 120A. In some examples, the clinician may enter instructions for a medical intervention for patient 4 into an app in device 120A, such as based on a status of a patient condition determined by IMD 10, external device 12, processing circuitry 14, wearable device 16, or any combination thereof, or based on other patient data known to the clinician. Device 120A then may transmit the instructions for medical intervention to another of computing devices 120A-120N (e.g., device 120B) located with patient 4 or a caregiver of patient 4. For example, such instructions for medical intervention may include an instruction to change a drug dosage, timing, or selection, to schedule a visit with the clinician, or to seek medical attention. In further examples, device 120B may generate an alert to patient 4 based on a status of a medical condition of patient 4 determined by IMD 10, which may enable patient 4 proactively to seek medical attention prior to receiving instructions for a medical intervention. In this manner, patient 4 may be empowered to take action, as needed, to address his or her medical status, which may help improve clinical outcomes for patient 4.

Figure 9:
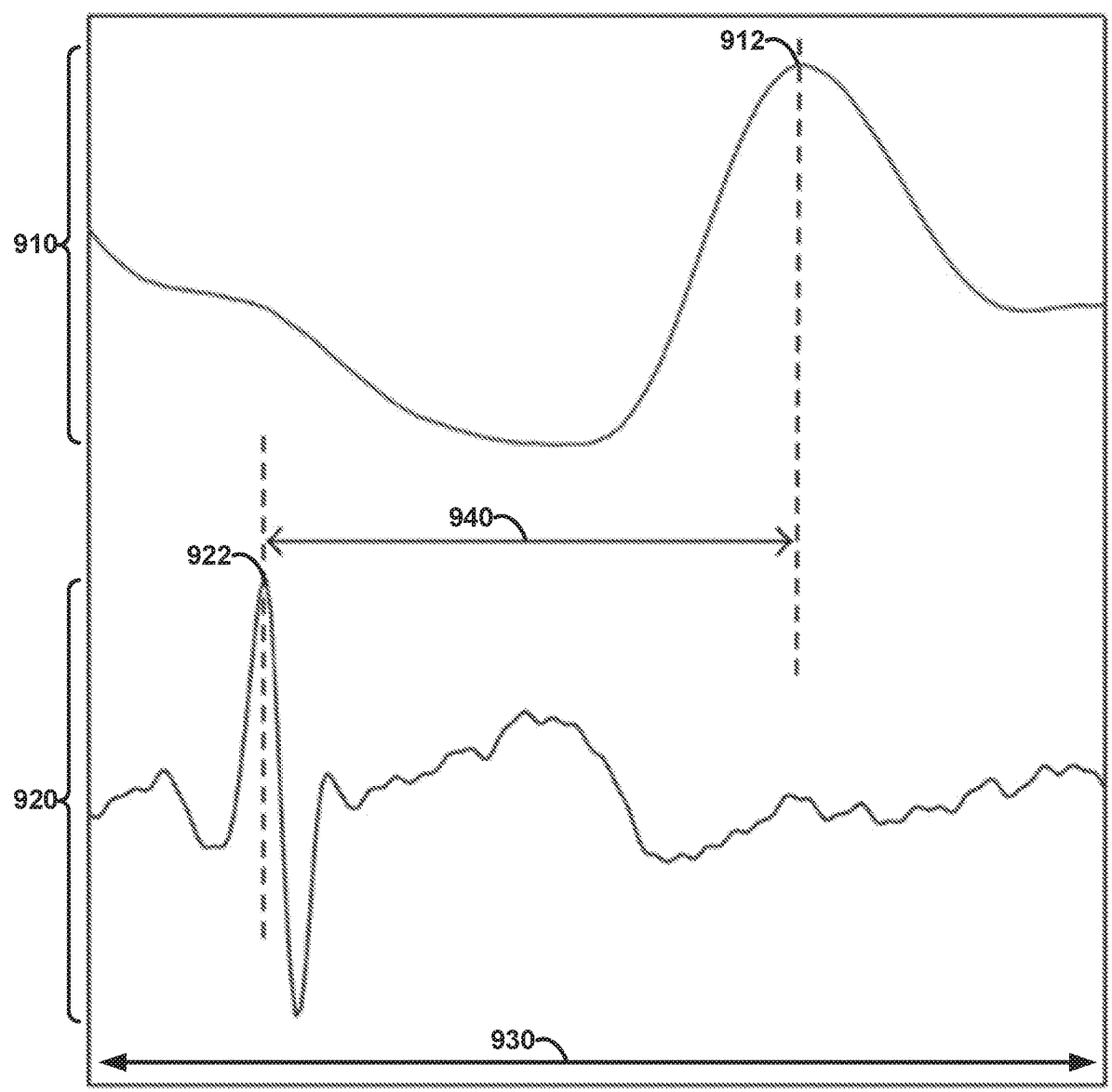
FIG. 9 is a graph illustrating a photoplethysmography (PPG) plot and an electrogram (EGM) plot, in accordance with one or more techniques of this disclosure.

FIG. 9 is a graph illustrating a PPG plot 910 and an EGM plot 920, in accordance with one or more techniques of this disclosure. In some examples, data representing the PPG plot 910 may be collected by wearable device 16 and data representing the EGM plot 920 may be collected by IMD 10. In some examples, one or both of PPG plot 910 and EGM plot 920 are recorded by one or more additional or alternative devices. PPG plot 910 and EGM plot 920 are recorded over the period of time 930. PPG plot 910 includes PPG peak 912. PPG peak 912 may represent a time in which an amount of blood in the tissue and peripheral vasculature of patient 4 proximate to wearable device 16 is at a maximum during a respective heart cycle that occurs during period of time 930. Additionally, EGM plot 920 includes R-wave 922 which represents a ventricular depolarization of the heart of patient 4 that causes wearable device 16 to collect data indicative of PPG peak 912. During the heart cycle of patient 4 represented by PPG plot 910 and EGM 920, the ventricles of patient 4 may depolarize at R-wave 922 to push blood into the vasculature of patient 4, the blood volume proximate to wearable device 16 peaking at PPG peak 912. Subsequently, the blood may return to the atria of the heart of patient 4.

An amount of time from R-wave 922 to PPG peak 912 may represent PTT interval 940. PTT interval 940 may be a representative amount of time that it takes a blood cell to flow from the heart of patient 4 to the peripheral vasculature/tissue proximate to wearable device 16 during a heart cycle. In some examples, a length of a PTT intervals is inversely correlated with a blood pressure of patient 4. For example, a first PTT interval having a first length may be indicative of a first blood pressure and a second PTT interval having a second length may be indicative of a second blood pressure. If the first length is greater than the second length, the first blood pressure may be less than the second blood pressure.

Additionally, if the first length is less than the second length, the first blood pressure may be greater than the second blood pressure.

Figure 10:
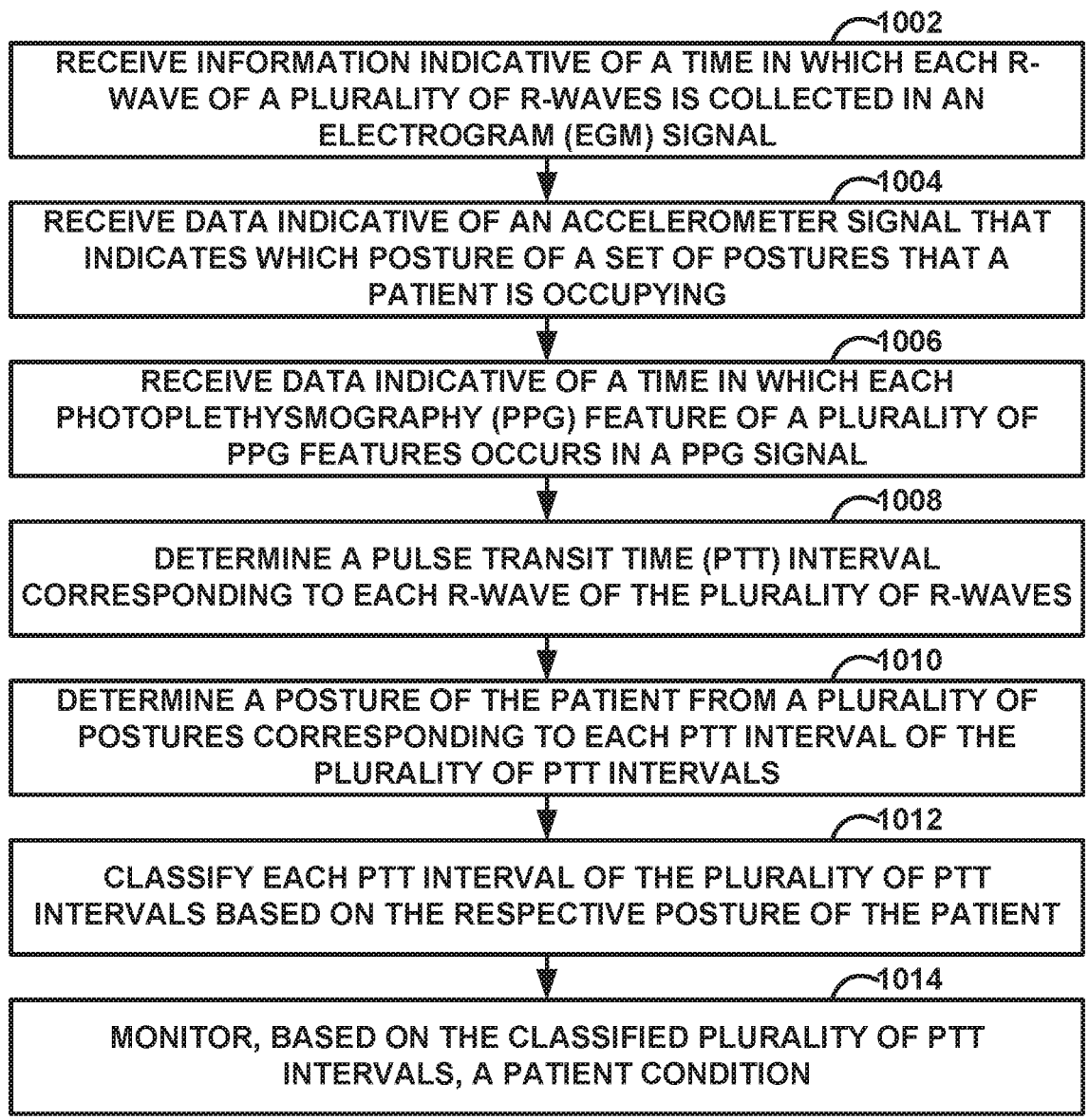
FIG. 10 is a flow diagram illustrating an example operation for monitoring a patient condition, in accordance with one or more techniques of this disclosure.

FIG. 10 is a flow diagram illustrating an example operation for monitoring a patient condition, in accordance with one or more techniques of this disclosure. FIG. 10 is described with respect to IMD 10, external device 12, processing circuitry 14, and wearable device 16 of FIGS. 1-8. However, the techniques of FIG. 10 may be performed by different components of IMD 10, external device 12, processing circuitry 14, and wearable device 16 or by additional or alternative medical device systems. Processing circuitry 14 is conceptually illustrated in FIG. 1 as separate from IMD 10, external device 12, and wearable device 16 but may be any one or combination of processing circuitry of IMD 10, processing circuitry of external device 12, and processing circuitry of wearable device 16. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10, external device 12, and/or wearable device 16 via a network.

IMD 10 may collect an EGM signal and an accelerometer signal and wearable device 16 may collect a PPG signal. In some cases, IMD 10 may collect at least a portion of the EGM signal over a same period of time that IMD 10 collects at least a portion of the accelerometer signal and wearable device 16 collects at least a portion of the PPG signal. In this way, the EGM signal, the accelerometer signal, and the PPG signal may overlap for at least a portion of time. Processing circuitry 14 may detect one or more PTT intervals based on the EGM signal collected by IMD 10 and the PPG signal collected by wearable device 16. Based on a trend in one or more PTT the one or more PTT intervals, processing circuitry may detect an occurrence or a worsening of a patient condition. In some examples, processing circuitry 14 may save one or more portions of the EGM signal, the accelerometer signal, and the PPG signal to a memory for further analysis based on an analysis of the EGM signal.

Processing circuitry 14 may receive data indicative of a time in which each R-wave of a plurality of R-waves is collected in an EGM signal (1002). In one example, the EGM signal (e.g., cardiac EGM) is collected via one or more electrodes of IMD 10. A cardiac EGM is a signal representative of electrical activity of the heart, measured by electrodes implanted within the body, and often within the heart itself. For example, a cardiac EGM may include P-waves (depolarization of the atria), R-waves (depolarization of the ventricles), and T-waves (repolarization of the ventricles), among other events. In some examples, the EGM signal may represent a sequence of heart cycles of patient 4, where each heart cycle of the sequence of heart cycles includes an R-wave of the plurality of R-waves. In some cases, processing circuitry 14 may receive data solely indicative of the time in which each R-wave of a plurality of R-waves is collected in the EGM signal. In some cases, processing circuitry 14 may receive data indicative of the entire EGM signal (e.g., each data point collected by IMD 10 for the EGM signal) or a portion of the EGM signal.

Processing circuitry 14 may receive data indicative of an accelerometer signal that indicates which posture of a set of postures that patient 4 is occupying (1004). In some examples, IMD 10 may collect the accelerometer signal. The accelerometer signal may include a vertical axis accelerometer signal vector, a lateral axis accelerometer signal vector, and a frontal axis accelerometer signal vector. The vertical axis accelerometer signal vector may represent an acceleration of patient 4 along a vertical axis, the lateral axis accelerometer signal vector may represent an acceleration of patient 4 along a lateral axis, and the frontal axis accelerometer signal vector may represent an acceleration of patient 4 along a frontal axis. In some cases, the vertical axis substantially extends along a torso of patient 4 when patient 4 from a neck of patient 4 to a waist of patient 4, the lateral axis extends across a chest of patient 4 perpendicular to the vertical axis, and the frontal axis extends outward from and through the chest of patient 4, the frontal axis being perpendicular to the vertical axis and the lateral axis. In some examples, processing circuitry 14 may be configured to determine a posture (e.g., supine, prone, lying on a left side, lying on a right side, sitting, and standing) of patient 4 based on the accelerometer signal. Additionally, or alternatively, in some examples, processing circuitry 14 may determine a body angle value of patient 4 based on the accelerometer signal which represents an angle of the body of patient 4 relative to the ground.

In some cases, processing circuitry 14 may receive data indicative of a time in which each PPG feature of a plurality of PPG features occurs in a PPG signal (1006). In some examples, wearable device 16 may collect the PPG signal using a light emitter and one or more light detectors. For example, the PPG signal may be indicative of a perfusion of blood to the dermis and subcutaneous tissue of patient 4. In this way, the PPG signal may represent a pulse of patient 4, where the PPG signal rises during a pulse and falls during periods between pulses. The light emitter of wearable device 16 may emit one or more photons and the light detector(s) of wearable device 16 may sense one or more photons emitted by the light detector and reflected by the tissue of patient 4. Based on the amount of light sensed by the light detectors of wearable device 16, processing circuitry (e.g., processing circuitry 90 of wearable device 16) may be able to determine an amount of blood present in the tissue proximate to wearable device 16, where the amount of blood peaks during a "pulse" occurring during each heart cycle of patient 4. In this way, the PPG signal may reflect each heartbeat of patient 4, with a PPG feature corresponding to a heartbeat. In some examples, the plurality of PPG features represents a plurality of PPG peaks, where a PPG peak represents a peak PPG value during a respective heart cycle.

Processing circuitry 14 may determine a PTT interval corresponding to each R-wave of the plurality of R-waves (1008) collected in the EGM signal. In some examples, processing circuitry 14 may determine the PTT interval corresponding to each R-wave of the plurality of R-waves by analyzing a relationship between the EGM signal (e.g., R-wave times) and the PPG signal (e.g., the set of PPG features). In some examples, processing circuitry 14 may determine a PTT interval relating to each R-wave of the plurality of R-waves in the EGM signal. For example, processing circuitry 14 may determine an amount of time between each R-wave of the plurality of R-waves and a respective PPG feature of the plurality of PPG features that occurs after the respective R-wave, the respective PPG feature occurring due to the ventricular depolarization denoted by the R-wave in the EGM signal. In this way, the respective PPG feature may represent a PPG peak. In some examples, a PPG feature that is recorded due to a ventricular depolarization marked by a first R-wave may occur before a second R-wave that is subsequent to the first R-wave, where the second R-wave is consecutive to the first R-wave.

Processing circuitry 14 may determine a posture of patient 4 from a plurality of postures corresponding to each PTT interval of the plurality of PTT intervals (1010). For example, processing circuitry 14 may determine the posture of patient 4 at a time in which each PTT interval of the plurality of PTT intervals occurs. Subsequently, processing circuitry 14 may classify each PTT interval of the plurality of PTT intervals based on the respective posture of patient 4 (1012). In some examples, to classify each PTT interval of the plurality of PTT intervals, processing circuitry 14 is configured to generate information identifying each PTT interval of the plurality of PTT intervals with the determined posture of 4 patient corresponding to the respective PTT interval. Processing circuitry 14 may store the information in a memory in communication with processing circuitry 14.

Processing circuitry 14 may monitor, based on the classified plurality of PTT intervals, a patient condition (1014). In some examples, to monitor the patient condition, processing circuitry 14 is configured to calculate, based on information identifying each PTT interval of the plurality of PTT intervals with the determined posture of the patient, a median of a set of PTT intervals which occur over a period of time preceding a present time. Each PTT interval of the set of PTT intervals may be classified as corresponding to a first group of postures of the plurality of postures. In this way, in monitoring the patient condition, processing circuitry 14 may only analyze PTT intervals which occur while patient 4 is in a specific one or more postures. For example, processing circuitry 14 may determine, based on the median of the set of PTT intervals, a trend. Processing circuitry 14 may calculate a set of PTT median values, wherein each PTT median value of the set of PTT median values is a median of a respective set of PTT intervals occurring over a respective period of time. To calculate the trend, processing circuitry 14 may determine whether the set of PTT median values represent a change in PTT interval length. In some cases, based on the identified trend, processing circuitry may determine a therapy to be delivered to patient 4, and/or output an alert prompting patient 4 to seek medical attention.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device system comprising:
    a medical device comprising:
        a plurality of electrodes configured to collect an electrogram (EGM) signal of a patient, wherein the EGM signal includes a plurality of depolarizations; and
        an accelerometer configured to collect an accelerometer signal that indicates which posture of a set of postures that the patient is occupying;
    a wearable device configured to collect a photoplethysmography (PPG) signal of the patient, wherein the PPG signal includes a plurality of PPG features indicating the occurrence of a cardiac pulse; and
    processing circuitry in communication with a memory, wherein the processing circuitry is configured to:
        determine a plurality of pulse transit time (PTT) intervals, wherein a PTT interval of the plurality of PTT intervals corresponds to each depolarization of the plurality of depolarizations, wherein each PTT interval of the plurality of PTT intervals represents an amount of time between a respective depolarization of the set of depolarizations and a PPG feature of the plurality of PPG features that occurs after the respective depolarization and before a subsequent depolarization of the plurality of depolarizations;
        determine, based on the accelerometer signal, a posture of the patient from a plurality of postures corresponding to each PTT interval of the plurality of PTT intervals;
        associate each PTT interval of the plurality of PTT intervals with one or more classifications, wherein the one or more classifications corresponding to each PTT interval of the plurality of PTT intervals indicate the posture of the patient corresponding to the respective PTT interval;
        select, from the plurality of PTT intervals, a set of PTT intervals based on the one or more associated classifications for each PTT interval of the plurality of PTT intervals, wherein each PTT interval of the set of PTT intervals is associated with a classification of the one or more classifications indicating at least one posture of a set of postures; and
        monitor, based on the selected set of PTT intervals, a patient condition.

2. The medical device of claim 1, wherein to associate each PTT interval of the plurality of PTT intervals with the one or more classifications, the processing circuitry is configured to:
    generate information identifying each PTT interval of the plurality of PTT intervals with the determined posture of the patient corresponding to the respective PTT interval; and
    store the information in the memory.

3. The medical device system of claim 2, wherein to monitor the patient condition, the processing circuitry is configured to:
calculate, based on the information identifying each PTT interval of the plurality of PTT intervals with the determined posture of the patient, a median of the set of PTT intervals, wherein the set of PTT intervals occur over a period of time preceding a present time; and
determine, based on the median of the set of PTT intervals, a trend.

4. The medical device system of claim 3, wherein the processing circuitry is further configured to:
calculate a set of PTT median values, wherein each PTT median value of the set of PTT median values is a median of a respective set of PTT intervals occurring over a respective period of time, and wherein to determine the trend, the processing circuitry is configured to:
determine whether the set of PTT median values represent a change in PTT interval length.

5. The medical device system of claim 1, wherein the accelerometer signal further indicates a motion level of the patient, and wherein the processing circuitry is further configured to:
determine, based on the accelerometer signal, a motion level of the patient corresponding to each PTT interval of the plurality of PTT intervals.

6. The medical device of claim 5, wherein the processing circuitry is further configured to:
determine whether the motion level of the patient corresponding to each PTT interval of the plurality of PTT intervals is lower than a threshold motion level; and
associate each PTT interval of the plurality of PTT intervals with one or more classifications indicating whether the respective PTT interval corresponds to a respective motion level that is lower than the threshold motion level.

7. The medical device of claim 6, wherein to associate each PTT interval of the plurality of PTT intervals with one or more classifications indicating whether the respective PTT interval corresponds to the respective motion level that is lower than the threshold motion level, the processing circuitry is configured to:
generate information identifying whether each PTT interval of the plurality of PTT intervals corresponds to the respective motion level that is lower than the threshold motion level; and
store the information in the memory.

8. The medical device of claim 6, wherein to monitor the patient condition, the processing circuitry is configured to:
calculate, based on the information identifying whether each PTT interval of the plurality of PTT intervals corresponds to the respective motion level that is lower than the threshold motion level, a median of the set of PTT intervals, wherein the set of PTT intervals occur over a period of time preceding a present time; and
determine, based on the median of the set of PTT intervals, a trend.

9. The medical device system of claim 1, wherein the wearable device is attached to one or both of a wrist of the patient or a finger of the patient.

10. The medical device system of claim 1, wherein the plurality of postures includes a supine position, a prone position, a lying on a side position, a sitting position, and a standing position.

11. The medical device system of claim 1, wherein the accelerometer represents a first accelerometer, wherein the accelerometer signal represents a first accelerometer signal, and wherein the wearable device further comprises:
a second accelerometer configured to collect a second accelerometer signal that indicates a motion level of an extremity of the patient on which the wearable device is worn;
determine whether the motion level of the extremity of the patient corresponding to each PTT interval of the plurality of PTT intervals is lower than a threshold extremity motion level; and
associate each PTT interval of the plurality of PTT intervals with one or more classifications, wherein the one or more classifications indicate whether the respective PTT interval corresponds to a respective extremity motion level that is lower than the threshold extremity motion level.

12. A method comprising:
collecting, using a plurality of electrodes of a medical device, an electrogram (EGM) signal of a patient, wherein the EGM signal includes a plurality of depolarizations;
collecting, using an accelerometer of the medical device, an accelerometer signal that indicates which posture of a set of postures that the patient is occupying;
collecting, using a wearable device, a photoplethysmography (PPG) signal of the patient, wherein the PPG signal includes a plurality of PPG features indicating the occurrence of a cardiac pulse;
determining, using processing circuitry in communication with a memory, a plurality of pulse transit time (PTT) intervals, wherein a PTT interval of the plurality of PTT intervals corresponds to each depolarization of the plurality of depolarizations, wherein each PTT interval of the plurality of PTT intervals represents an amount of time between a respective depolarization of the set of depolarizations and a PPG feature of the plurality of PPG features that occurs after the respective depolarization and before a subsequent depolarization of the plurality of depolarizations;
determining, based on the accelerometer signal, a posture of the patient from a plurality of postures corresponding to each PTT interval of the plurality of PTT intervals;
associating each PTT interval of the plurality of PTT intervals with one or more classifications corresponding to each PTT interval of the plurality of PTT intervals, wherein the one or more classifications indicate the posture of the patient corresponding to the respective PTT interval;
selecting, from the plurality of PTT intervals, a set of PTT intervals based on the one or more associated classifications for each PTT interval of the plurality of PTT intervals, wherein each PTT interval of the set of PTT intervals is associated with a classification of the one or more classifications indicating at least one posture of a set of postures; and
monitoring, based on the selected set of PTT intervals, a patient condition.

13. The method of claim 12, wherein associating each PTT interval of the plurality of PTT intervals with the one or more classifications comprises:
generating information identifying each PTT interval of the plurality of PTT intervals with the determined posture of the patient corresponding to the respective PTT interval; and
storing the information in the memory.

14. The method of claim 13, wherein monitoring the patient condition comprises:
- calculating, based on the information identifying each PTT interval of the plurality of PTT intervals with the determined posture of the patient, a median of the set of PTT intervals, wherein the set of PTT intervals occur over a period of time preceding a present time; and
- determining, based on the median of the set of PTT intervals, a trend.

15. The method of claim 14, further comprising:
- calculating a set of PTT median values, wherein each PTT median value of the set of PTT median values is a median of a respective set of PTT intervals occurring over a respective period of time, and wherein to determining the trend comprises:
- determining whether the set of PTT median values represent a change in PTT interval length.

16. The method of claim 12, wherein the accelerometer signal further indicates a motion level of the patient, and wherein the method further comprises:
- determining, based on the accelerometer signal, a motion level of the patient corresponding to each PTT interval of the plurality of PTT intervals.

17. The method of claim 16, wherein the method further comprises:
- determining whether the motion level of the patient corresponding to each PTT interval of the plurality of PTT intervals is lower than a threshold motion level; and
- associating each PTT interval of the plurality of PTT intervals with one or more classifications indicating whether the respective PTT interval corresponds to a respective motion level that is lower than the threshold motion level.

18. The method of claim 17, wherein associating each PTT interval of the plurality of PTT intervals with one or more classifications indicating whether the respective PTT interval corresponds to the respective motion level that is lower than the threshold motion level comprises:
- generating information identifying whether each PTT interval of the plurality of PTT intervals corresponds to the respective motion level that is lower than the threshold motion level; and
- storing the information in the memory.

19. The method of claim 17, wherein monitoring the patient condition comprises:
- calculating, based on the information identifying whether each PTT interval of the plurality of PTT intervals corresponds to the respective motion level that is lower than the threshold motion level, a median of the set of PTT intervals, wherein the set of PTT intervals occur over a period of time preceding a present time; and
- determining, based on the median of the set of PTT intervals, a trend.

20. A non-transitory computer-readable medium comprising instructions for causing one or more processors to:
- collect, using a plurality of electrodes of a medical device, an electrogram (EGM) signal of a patient, wherein the EGM signal includes a plurality of depolarizations;
- collect, using an accelerometer of the medical device, an accelerometer signal that indicates which posture of a set of postures that the patient is occupying;
- collect, using a wearable device, a photoplethysmography (PPG) signal of the patient, wherein the PPG signal includes a plurality of PPG features indicating the occurrence of a cardiac pulse;
- determine, using processing circuitry in communication with a memory, a plurality of pulse transit time (PTT) intervals, wherein a PTT interval of the plurality of PTT intervals corresponds to each depolarization of the plurality of depolarizations, wherein each PTT interval of the plurality of PTT intervals represents an amount of time between a respective depolarization of the set of depolarizations and a PPG feature of the plurality of PPG features that occurs after the respective depolarization and before a subsequent depolarization of the plurality of depolarizations;
- determine, based on the accelerometer signal, a posture of the patient from a plurality of postures corresponding to each PTT interval of the plurality of PTT intervals;
- associate each PTT interval of the plurality of PTT intervals with one or more classifications, wherein the one or more classifications corresponding to each PTT interval of the plurality of PTT intervals indicate the posture of the patient corresponding to the respective PTT interval;
- select, from the plurality of PTT intervals, a set of PTT intervals based on the one or more associated classifications for each PTT interval of the plurality of PTT intervals, wherein each PTT interval of the set of PTT intervals is associated with a classification of the one or more classifications indicating at least one posture of a set of postures; and
- monitor, based on the selected set of PTT intervals, a patient condition.

\* \* \* \* \*